United States Patent
Filges et al.

(10) Patent No.: US 9,260,546 B2
(45) Date of Patent: Feb. 16, 2016

(54) PRODUCING AQUEOUS SOLUTIONS OF VINYLLACTAM POLYMERS AND POWDERS THEREOF

(71) Applicant: BASF SE, Ludwigshafen (DE)

(72) Inventors: Ulrich Filges, Neustadt (DE); Bernd de Potzolli, Bad Dürkheim (DE); Andy Wolff, Böhl-Iggelheim (DE)

(73) Assignee: BASF SE, Ludwigshafen (DE)

( * ) Notice: Subject to any disclaimer, the term of this patent is extended or adjusted under 35 U.S.C. 154(b) by 14 days.

(21) Appl. No.: 13/961,087

(22) Filed: Aug. 7, 2013

(65) Prior Publication Data

US 2014/0044662 A1  Feb. 13, 2014

Related U.S. Application Data

(60) Provisional application No. 61/680,745, filed on Aug. 8, 2012.

(51) Int. Cl.
| | |
|---|---|
| *C08F 26/10* | (2006.01) |
| *A61K 8/81* | (2006.01) |
| *A61Q 5/06* | (2006.01) |
| *A61Q 19/00* | (2006.01) |
| *A61K 8/04* | (2006.01) |
| *C08F 220/56* | (2006.01) |

(52) U.S. Cl.
CPC .............. *C08F 26/10* (2013.01); *A61K 8/042* (2013.01); *A61K 8/817* (2013.01); *A61K 8/8176* (2013.01); *A61Q 5/06* (2013.01); *A61Q 19/00* (2013.01); *C08F 220/56* (2013.01)

(58) Field of Classification Search
CPC .............................. A61K 8/8176; C08F 26/10
See application file for complete search history.

(56) References Cited

U.S. PATENT DOCUMENTS

| | | | |
|---|---|---|---|
| 2,335,454 A | 11/1943 | Schuster et al. | |
| 2,821,519 A | 1/1958 | Glickman | |
| 2,872,433 A | 2/1959 | Glickman | |
| 4,053,696 A | 10/1977 | Herrle et al. | |
| 5,262,171 A | 11/1993 | Login et al. | |
| 6,331,333 B1 | 12/2001 | Wu et al. | |
| 6,498,231 B2 | 12/2002 | Tomihisa et al. | |
| 6,592,900 B1 | 7/2003 | Buhler et al. | |
| 7,666,935 B2 | 2/2010 | Bohrer et al. | |
| 2008/0139724 A1* | 6/2008 | Kolter et al. | ............ 524/421 |
| 2009/0124775 A1* | 5/2009 | Miyai et al. | ............ 526/264 |
| 2011/0158929 A1 | 6/2011 | Kim et al. | |
| 2011/0257339 A1* | 10/2011 | Fischer et al. | ............ 525/185 |
| 2014/0044662 A1 | 2/2014 | Filges et al. | |

FOREIGN PATENT DOCUMENTS

| | | | |
|---|---|---|---|
| DE | 102004049344 | 4/2006 | |
| DE | 102005005974 | 8/2006 | |
| DE | 112005002719 | 12/2007 | |
| DE | WO 2010/072640 | * 7/2010 | ............ C08F 6/02 |
| EP | 0873130 | 10/1998 | |
| EP | 1083884 | 3/2001 | |
| EP | 1950230 | 7/2008 | |
| GB | 836831 | 6/1960 | |
| WO | WO 93/16114 | * 1/1993 | ............ C08F 6/10 |
| WO | WO-93/16114 | 8/1993 | |
| WO | WO-97/25052 | 7/1997 | |
| WO | WO-00/59478 | 10/2000 | |
| WO | WO-2009/024457 | 2/2009 | |
| WO | WO-2010/052008 | 5/2010 | |
| WO | WO-2010/072640 | 7/2010 | |
| WO | WO-2014/023602 | 2/2014 | |

OTHER PUBLICATIONS

PCT International Search Report in PCT/EP2013/065942, mailed Oct. 29, 2013, 3 pages.
Buehler, Volker, Polyvinylpyrrolidone—Excipients for Phamaceuticals, *Springer* 2005, 34-35.

* cited by examiner

*Primary Examiner* — Anna Falkowitz
(74) *Attorney, Agent, or Firm* — Servilla Whitney LLC

(57) ABSTRACT

Described is a process for producing aqueous solutions of vinyllactam polymers and solids obtainable therefrom by drying, especially polyvinylpyrrolidone, said process comprising using one or more sulfur components selected from the group consisting of sulfur dioxide, sulfurous acid and one or more salts of sulfurous acid, to reduce residual monomer. Also described are vinyllactam polymers obtainable by the process which have good stability in storage, the use of these vinyllactam polymers, and articles of manufacture and preparations comprising these vinyllactam polymers or obtained by use thereof.

12 Claims, No Drawings

PRODUCING AQUEOUS SOLUTIONS OF VINYLLACTAM POLYMERS AND POWDERS THEREOF

CROSS-REFERENCE TO RELATED APPLICATIONS

This application claims the benefit under 35 U.S.C. §119 (e) to U.S. Provisional Application No. 61/680,745, filed Aug. 8, 2012, the entire content of which is incorporated herein by reference in its entirety.

BACKGROUND

Producing N-vinylpyrrolidone polymers by free-radical polymerization is known. The polymerization mechanism under various conditions is described for example in Polymer Journal, 17, 143-152 (1985). The patent literature describes not only polymerizations in organic solvents as in alcoholic solution in U.S. Pat. No. 4,053,696 for example but also in aqueous solution as described in U.S. Pat. No. 2,335,454 for example.

Polymerization in organic solvents as described in U.S. Pat. No. 4,053,696 generally leads to products comprising only a relatively low proportion of impurities such as formic acid. But this process has the immense disadvantage that the polymerization first has to be carried out in a solvent such as isopropanol. Only after the polymerization has ended, a costly and inconvenient distillation process has to be used to distill off the solvent e.g. the isopropanol and replace it with water. This generates comparatively large amounts of solvent, which either have to be disposed of or purified by distillation. This leads to long occupancy of the polymerization reactor and an unfavorable space-time yield.

Polymerization of N-vinylpyrrolidone in aqueous solution, by contrast, is usually carried out in the presence of hydrogen peroxide as initiator, as described in U.S. Pat. No. 2,335,454 for example. The molecular weight of the polyvinylpyrrolidone here depends on the hydrogen peroxide concentration in that low molecular weights are the result of high hydrogen peroxide concentrations, and vice versa. But high hydrogen peroxide quantities promote the formation of formic acid in the aqueous system; polymers thus obtained have a distinct yellow coloration even in the as-polymerized state.

DE 11 2005 002 719 describes a process for producing aqueous polyvinylpyrrolidone polymer solutions. A process for handling vinylpyrrolidone polymer solutions is also disclosed. This process provides polymers of low HAZEN color number (the Hazen color number corresponds to the "cobalt-platinum color number" and is known per se to a person skilled in the art, for example from the industrial standard DIN ISO 6271-1). The polymer solutions obtained by this process have the immense disadvantage of a high formic acid content and of gradually discoloring in the course of storage. The formic acid is by-produced as an undesired secondary component during the polymerization. The polymer obtained is unsuitable for frequent purposes, especially when PVP powders are produced from the solutions by spray drying. There are formic acid limits to be heeded for use in pharmaceutical and cosmetic products in particular. For instance, a formic acid limit of not more than 0.5 weight percent is prescribed in the "Povidones" monograph in the European Pharmacopeia, and even in cosmetic formulations, the formic acid fraction present as preservative must not exceed a limit of 0.5 weight percent. As mentioned, the initially colorless solutions discolor on prolonged storage.

But this property of discolorations is precisely what is undesirable for cosmetic formulations, especially when transparent, colorless hair gels are to be produced therefrom.

Bühler reports color changes in aqueous PVP solutions especially after storage or heating, for example in the course of sterilization. The resulting yellow to yellowish brown coloration results from oxidation due to atmospheric oxygen. This, according to Bühler, can be avoided by adding suitable antioxidants. Bühler names cysteine and sodium sulfite as such antioxidants (Volker Bühler, "Polyvinylpyrrolidone—Excipients for Pharmaceuticals", Springer, 2005, pages 34 and 35 regarding stability in solid and liquid dosage forms).

The peroxides from the polymerization and formed directly thereafter have the disadvantageous effect of being at least partly consumed even on addition to the polymer thus reducing the protection and the length of storage. To compensate this effect, therefore, comparatively large amounts of antioxidant have to be used.

The oxidation sensitivity of polymers such as PVP, the macroscopically visible and measurable effects of oxidation and also proposed measures to control and inhibit oxidation has been described in many publications (see for example Bühler in the above-cited publication; Kline in Modern Plastics, 1945, November, from page 157; Reppe in the monograph regarding PVP, Chemie Publishers, Weinheim, 1954, page 24; EP-B 873 130; U.S. Pat. No. 6,331,333; U.S. Pat. No. 6,498,231; Staszewska in "Die Angewandte Makromolekulare Chemie", 1983, 118, pages 1 to 17).

U.S. Pat. No. 2,821,519 describes a process for stabilizing PVP via addition of hydrazine and derivatives thereof. Hydrazines are toxicologically concerning and undesired in polyvinylpyrrolidones, N-vinylpyrrolidone copolymers and polymers of N-vinylpyrrolidone derivatives in particular.

EP-B 1 083 884 describes a process for stabilizing polyvinylpyrrolidones against peroxide formation. Aqueous solutions of the polymers are admixed with very small amounts of heavy metal salts or with peroxide-cleaving enzymes. These remain in the product. Suitable heavy metals are manganese, zinc, cobalt and especially copper.

However, the use of the heavy metals proposed is disadvantageous by reason of possible accumulation in the body. The use of enzymes is disadvantageous for cost and stability reasons.

GB 836,831 discloses a process for stabilizing polyvinylpyrrolidones against discoloration wherein solutions of the polymers are treated with sulfur dioxide, sulfurous acid or alkali metal sulfites. It is disclosed to add the sulfur compound by mixing it at room temperature into polymer solutions obtained by dissolving dry polymeric powder in water. The sulfur compound is used as a reducing agent which is said to offer protection from yellowing at high temperatures to which the polymer solution is exposed in the course of undergoing sterilization or drying.

DE 10 2005 005 974 discloses that in the process known from GB 836,831 the peroxide buildup by storage occurs to an even greater degree than in untreated polymers. DE 10 2005 005 974 discloses a process wherein the polyvinylpyrrolidones are first treated with sulfur dioxide, sulfurous acid or alkali metal salts thereof and then with a free-radical scavenger. The sulfur-containing reagents are added after the postpolymerization and after any acidic hydrolysis and immediately before the optional drying, incorporated by stirring and serve as reducing agent. Antioxidants have to be used in addition to achieve any stabilization.

Residual monomer is reduced in the prior art by repeated addition of minor initiator portions to the polymer solution after the polymerization and postpolymerization (DE 11 2005

002 719). This described aftertreatment of DE 11 2005 002 719 involving renewed addition of initiator, however, leads to elevated and unwanted formate contents.

Residual monomer reduction by addition of organic and inorganic acids is known from WO 93/16114 A1. It discloses reduction to pH below 5 for acidic hydrolysis of vinyllactams to free lactams, such as vinylpyrrolidone to 2-pyrrolidone.

SUMMARY

The problem addressed by the present invention was that of providing a simple process for producing aqueous PVP solutions of low formic acid/formate content and of avoiding undesired, for example toxicologically concerning, additions such as metals, enzymes or antioxidants, simultaneously coupled with high color stability during storage.

One or more embodiments of the present invention relate to a process for producing aqueous solutions of vinyllactam polymers and solids obtainable therefrom by drying, especially polyvinylpyrrolidone, said process comprising using one or more sulfur components selected from the group consisting of sulfur dioxide, sulfurous acid and one or more salts of sulfurous acid, to reduce residual monomer. Embodiments of the invention also relate to vinyllactam polymers obtainable by the process, the use of such vinyllactam polymers, and articles of manufacture and preparations comprising these vinyllactam polymers or obtained by use thereof. In some embodiments, these vinyllactam polymer have good stability in storage.

DETAILED DESCRIPTION

One or more embodiments of the present invention pertain to a process for producing a polymer comprising the steps of (general embodiment A 1):
a) polymerizing monomers via free-radical polymerization in a liquid,
b) optionally using a base as pH regulator during this polymerization,
c) optional postpolymerization,
d) optional purifying by stripping with gas, thermal distillation and/or steam distillation,
e) treating the polymer with a sulfur component selected from the group consisting of sulfurous acid, sulfur dioxide and one or more salts of sulfurous acid, wherein the pH of a water-containing phase with which the polymer comes into contact during the treatment with the sulfur component has a value of less than 6, and keeping the polymer in contact with the water-containing phase comprising the sulfur component at this pH for a period between 10 minutes and 8 hours, and then optional repeat of step d),
f) optionally adding a base to set a desired pH,
g) optional purification using filtration for example, and
h) optionally drying the liquid-containing polymer to form a solid material.

Preferably, process step e) comprises treating the polymer with a sulfur component selected from the group consisting of sulfurous acid, sulfur dioxide and one or more salts of sulfurous acid, so the pH of a water-containing phase with which the polymer comes into contact during the treatment has a value of less than 6, preferably less than 5.5, more preferably less than 5, most preferably less than 4, and keeping the polymer in contact with the water-containing phase comprising the sulfur component at this pH for a period between 10 minutes and 8 hours, preferably at least 30 minutes and not more than 4 hours, and then optional repeat of step d).

A further embodiment of the present invention is a process to produce a vinyllactam polymer having K values of 10 to 150, comprising steps a) to h) (general embodiment A 2):
a) polymerizing one or more N-vinyllactams and optionally further monomers via free-radical polymerization with a free-radical initiator in an aqueous liquid, wherein the polymerization process is performed as batch process, as semi-batch process or as continuous process,
b) using at least one base to maintain the pH during the polymerization in a range from 5 to 11;
c) optional postpolymerization, wherein further initiator can be added;
d) optional purification by stripping with gas, thermal distillation and/or steam distillation;
e) treating the vinyllactam polymer with a sulfur component selected from the group consisting of sulfurous acid, sulfur dioxide and one or more salts of sulfurous acid, wherein the pH of a water-containing phase with which the polymer comes into contact during the treatment with the sulfur component has a value of less than 6, and keeping the polymer in contact with the water-containing phase comprising the sulfur component at this pH for a period between 10 minutes and 5 hours, and then optional repeat of step d);
f) optionally adding at least one base to set a desired pH in the range from 4 to 9;
g) optional purification by filtering;
h) optional drying to form a free-flowing powder.

A further, preferred embodiment 1 is a process to produce a vinyllactam polymer, preferably a vinylpyrrolidone polymer and more preferably polyvinylpyrrolidone, having K values of 10 to 150, preferably 15 to 130, more preferably 20 to 95, even more preferably 20 to 50 and especially of 25 to 35, comprising steps a) to h):
a) polymerizing one or more N-vinyllactams, preferably at least vinylpyrrolidone, and optionally further monomers, more preferably only vinylpyrrolidone as monomer, via free-radical polymerization with a free-radical initiator, preferably hydrogen peroxide with a copper salt to control free-radical formation, in an aqueous liquid, preferably in water, wherein the polymerization process is preferably performed as batch process,
b) using at least one base, preferably selected from the group consisting of ammonia, ammonium carbonate, ammonium hydrogencarbonate, 2-amino-2-methyl-1-propanol, tris(hydroxymethyl)aminomethane, 2-amino-1-butanol, 2-amino-2-ethyl-1,3-propanediol, 2-amino-2-methyl-1,3-propanediol, triethanolamine, diethanolamine, monoethanolamine and triethylamine, and more preferably selected from the group consisting of ammonia, ammonium carbonate, ammonium hydrogencarbonate and 2-amino-2-methyl-1-propanol (AMP 95), to maintain the pH during the polymerization in a range from 5 to 11, preferably 5.5 to 10.5, more preferably 6 to 9.5 and most preferably from 6.5 to 9, for example at 7, 7.5, 8 or 8.5;
c) optional postpolymerization, wherein further initiator, preferably hydrogen peroxide, can be added as free-radical former with a copper salt to control free-radical formation, but preferably no further initiator is added;
d) purification by stripping with gas, thermal distillation and/or steam distillation, preferably by steam distillation when the liquid is water or quite overwhelmingly water or by thermal distillation and subsequent steam distillation when the liquid is a mixture of water and major amounts of organic solvent or essentially organic solvent;
e) treating the polymer with sulfur component, wherein the sulfur component is selected from the group consisting of sulfurous acid, sulfur dioxide and one or more salts of sulfurous acid, so the pH of a water-containing phase with which the polymer comes into contact in the course of the treatment has a value of less than 6, preferably less than 5 and more preferably less than 4, and keeping the polymer in contact with the water-containing phase comprising the sulfur component at this pH for a period between 10 minutes and 5 hours, preferably at least 30 minutes and not more than 2 hours, and then optionally repeating step d), preferably with repeat of step d), f) optionally adding at least one base, preferably selected from the group consisting of ammonia, ammonium (hydrogen)carbonate, 2-amino-2-methyl-1-propanol, tris(hydroxymethyl)aminomethane, 2-amino-1-butanol, 2-amino-2-ethyl-1,3-propanediol, 2-amino-2-methyl-1,3-propanediol, triethanolamine, diethanolamine, monoethanolamine and triethylamine, preferably selected from ammonia, 2-amino-2-methyl-1-propanol, tris(hydroxymethyl)aminomethane, triethanolamine and triethylamine, more preferably selected from ammonia, 2-amino-2-methyl-1-propanol and tris(hydroxymethyl)aminomethane to set a desired pH in the range from 4 to 9, preferably 5 to 8 and more preferably 6 to 8, such as for example 4.5, 5, 5.5, 6, 6.5, 7, 7.5, 8 or 8.5;

g) optional purification by filtration, preferably using a cloth filter, h) optionally drying, preferably by a spray-drying process, the liquid-containing polymer to form a solid material, preferably a free-flowing powder.

In a further preferred embodiment 2, step f) in embodiment 1) is carried out, preferably by using ammonia or 2-amino-2-methyl-1-propanol (AMP 95) as base.

In a further preferred embodiment 3, step g) in embodiment 1) is carried out.

In a further preferred embodiment 4, step h) in embodiment 1) is carried out, preferably by using a spray-drying process, to obtain a dry polymeric powder.

In a further preferred embodiment 5, step c) in embodiment 1) is not carried out.

In a further, particularly preferred embodiment 6, steps f), g) and h) are carried out in embodiment 1) and step c) is not carried out in embodiment 1), preferably with ammonia or 2-amino-2-methyl-1-propanol (AMP 95) as base in step f), preferably a mechanical filter in step g) and preferably a spray-drying process in step h).

In a further, particularly preferred embodiment 7), steps f), g) and h) are and step c) is not carried out in embodiment 1), and step e) is followed by a further purifying step d), preferably via steam distillation in step d), preferably with ammonia or 2-amino-2-methyl-1-propanol (AMP 95) as base in step f), preferably a mechanical filter in step g) and preferably with a spray-drying process in step h).

In further, very particularly preferred embodiments 8 to 14, embodiments 1 to 7 are each carried out using ammonium hydrogencarbonate as base in step b), which is preferably only added at the start of the polymerization reaction.

In further, very particularly preferred embodiments 15 to 21, embodiments 1 to 7 are each carried out using ammonia as base in step b), which is preferably only added at the start of the polymerization reaction.

In further, very particularly preferred embodiments 22 to 42, embodiments 1 to 21 are each carried out using sulfur dioxide in aqueous solution as sulfur component.

In further, especially preferred embodiments 43 to 84, embodiments 1 to 42 are each carried out such that the process only consists of steps a) to h) including the repeated step d) following step e).

One or more embodiments of the present invention also provide a polymer obtainable by the process of the invention, preferably by one of embodiments 1 to 84, more preferably by one of embodiments 22 to 42 or 64 to 84, even more preferably by one of embodiments 29 to 42 or 71 to 84, especially by one of embodiments 29 to 35 or 71 to 77 such as 13, 14, 20, 21, 27, 28, 34, 35, 41, 42, 48, 49, 55, 56, 62, 63, 69, 70, 76, 77, 83 and 84, with high stability regarding physical parameters such as especially color, odor, clarity and viscosity of a solution of the polymer.

One or more embodiments of the present invention also provide for the use of the polymer obtained according to the invention and/or of a polymer obtainable by the process of the present invention as an excipient or active ingredient in the area of cosmetics such as especially hair cosmetics such as hair gels, in the area of pharmaceuticals, animal feed, animal health, engineering such as especially membranes for separation of materials, biomedical engineering such as especially for production of membranes for purification of liquids/fluids such as blood and water such as especially dialysis membranes, in the area of crop protection, beverage technology or food technology.

One or more embodiments of the present invention also provide medicinal products comprising polymer obtained according to one or more embodiments of the present invention and/or polymer obtainable by the process of the present invention.

One or more embodiments of the present invention likewise provide compositions for hair care and setting, preferably hair gels, especially colorless and clear hair gels, comprising polymer obtained according to one or more embodiments of the present invention and/or polymer obtainable by the process of the present invention.

One or more embodiments of the present invention likewise provide membranes, preferably for purification of liquids/fluids such as blood and water, especially dialysis membranes, comprising polymer obtained according to one or more embodiments of the present invention and/or polymer obtainable by the process of the present invention.

"Sulfur component" in the context of the present invention refers to a substance selected from the group consisting of sulfurous acid, sulfur dioxide and one or more salts of sulfurous acid. "A" sulfur component refers to an individual compound or two or more compounds selected from the designated group when it is not unambiguously clear from the description that only "a single" sulfur component is meant.

An "aqueous solution of sulfur dioxide" is usually—but chemically wrongly—designated "sulfurous acid". The designations "sulfur dioxide in aqueous solution", "an aqueous solution of sulfur dioxide" and "sulfurous acid" are accordingly designations for one and the same substance.

The process of one or more embodiments of the present invention can in principle be used to obtain all homo- and copolymers of N-vinyllactams.

The term "polymer" comprises for example linear, water-solubly branched or water-insolubly branched polymers. The term "water-insolubly branched polymer" also comprises the so-called popcorn polymers which in English are referred to as "proliferous polymers" or, as in the case of polyvinylpyrrolidone, as PVPP.

"Branched", "branching", "crosslinked", "crosslinking" is used interchangeably in the context of the present invention and refers to polymers having one or more than one site of branching.

"Polymer" also comprises the copolymers, graft homo- or graft copolymers, which can each be present as linear or solubly crosslinked, especially water-solubly crosslinked or insolubly crosslinked, especially water-solubly crosslinked, polymers.

"Polymer" can be present in any form, for example as di- or multi-block polymers, as well as in star, brush or hyperbranched form or as dendrimer.

Preferred polymers are linear, uncrosslinked polymers, more preferably water-soluble, linear, uncrosslinked polymers.

Polymers of one or more embodiments of the present invention comprise one or more monomers a), optionally one or more monomers b) and also optionally one or more crosslinking monomers c), i.e., they were obtained by polymerizing the monomers mentioned and may further comprise residual levels of monomers.

Monomers a) are selected from:

N-vinyllactams such as N-vinylpyrrolidone, N-vinylpiperidone, N-vinylcaprolactam, their C1 to C8-alkyl-substituted derivatives such as 3-methyl-, 4-methyl- and 5-methyl-N-vinylpyrrolidone, N-vinylamides such as N-vinylformamide and its N-vinylamine obtainable by hydrolysis following polymerization, N-vinyl-N-methylacetamide, amines such as N-vinyl- or allyl-substituted heterocyclic compounds, preferably N-vinylpyridine, N-allylpyridine, N-vinylimidazoles, which can also be substituted in 2-, 4- or 5-position with C1-C4-alkyl, especially methyl or phenyl, such as 1-vinylimidazole, 1-vinyl-2-methylvinylimidazole and also quaternized analogs thereof such as 3-methyl-1-vinylimidazolium chloride, 3-methyl-1-vinylimidazolium methosulfate, N—C1- to C24-alkyl-substituted diallylamines and quaternized analogs thereof such as diallylammonium chloride and diallyldimethylammonium chloride.

Preferred monomers a) are vinyllactams such as N-vinylpyrrolidone, 3-methyl-N-vinylpyrrolidone, 4-methyl-N-vinylpyrrolidone, 5-methyl-N-vinylpyrrolidone, N-vinylpiperidone and N-vinylcaprolactam, vinyl acetate and also the vinyl alcohol obtainable by hydrolysis following polymerization, vinylamides such as vinylformamide and also the vinylamine obtainable by hydrolysis following polymerization, N-vinylimidazole, 1-vinyl-3-methylimidazolium chloride, 1-vinyl-3-methylimidazolium sulfate, and vinylmethylamide and also derivatives thereof. Very particularly preferred monomers a) are N-vinylpyrrolidone, N-vinylcaprolactam, vinyl acetate, vinylformamide and also the vinylamine obtainable by hydrolysis following polymerization and also N-vinylimidazole.

Polymers according to one or more embodiments of the present invention always comprise at least one vinyllactam monomer selected from the group of monomers a).

Polymers according to one or more embodiments of the present invention may be homopolymers as well as copolymers of two or more monomers a), for example copolymers of N-vinylpyrrolidone and N-vinylimidazole, copolymers of N-vinylpyrrolidone and N-vinylformamide, copolymers of N-vinylpyrrolidone and N-vinylcaprolactam, copolymers of N-vinylpyrrolidone, N-vinylcaprolactam and N-vinylimidazole or copolymers of N-vinylpyrrolidone and N-vinylimidazole.

Useful monomers b) include all monomers mentioned in WO 2010/072640 A1 as "monomer b)" at page 6 line 8 to page 8 line 17, which passage is hereby fully incorporated herein by reference.

Preferred monomers b) are maleic acid, maleic anhydride, isopropylmethacrylamide, acrylamide, methacrylamide, 2-hydroxyethylacrylamide and 2-hydroxyethylmethacrylamide, also vinyl esters of aliphatic C2-C18-carboxylic acids such as vinyl acetate and also the vinyl alcohol obtainable by hydrolysis following polymerization, vinyl propionate, vinyl butyrate, vinyl laurate, vinyl stearate, vinyl neodecanoate VEOVA 9 and VEOVA 10, also dimethylaminoethyl(meth) acrylate and dimethylaminoethyl(meth)acrylamide and quaternized analogs thereof and also diallyldimethylammonium chloride.

Very particularly preferred monomers b) are methacrylamide, vinyl acetate and also the vinyl alcohol obtainable by hydrolysis following polymerization, vinyl propionate, vinyl neodecanoate VEOVA 9 and VEOVA 10, dimethylaminoethyl(meth)acrylate and dimethylamino-ethyl(meth)acrylamide and quaternized analogs thereof and also diallyldimethylammonium chloride.

Polymers that are copolymers and comprise monomers b) may comprise one or more monomers b). Typically, however, not more than five different monomers b) are present in any one copolymer.

The preferred polymers include furthermore copolymers comprising one or more monomers a) and one or more monomers b).

Crosslinking monomers c) ("crosslinkers") are monomers having two or more free-radically polymerizable groups. Suitable crosslinking monomers c) are described for example in WO2009/024457 at page 7 line 1 to page 9 line 2, which passage is hereby expressly incorporated herein by reference.

Particular preference for use as crosslinking monomers c) is given to pentaerythritol triallyl ether, methylenebisacrylamide, N,N'-divinylethyleneurea, divinylbenzene, ethylenebis-N-vinylpyrrolidone, 3-vinyl-N-vinylpyrrolidone, 4-vinyl-N-vinylpyrrolidone, 5-vinyl-N-vinylpyrrolidone, allyl(meth)acrylate, triallylamine, acrylic esters of glycol, butanediol, trimethylolpropane and glycerol and also acrylic esters of ethoxylated and/or epichlorohydrinated glycol, butanediol, trimethylolpropane and glycerol. Very particularly preferred crosslinkers are pentaerythritol triallyl ether, methylenebisacrylamide, N,N'-divinylethyleneurea, triallylamine and ethylenebis-N-vinylpyrrolidone, especially N,N'-divinylethyleneurea for water-insolubly crosslinked polymers and especially pentaerythritol triallyl ether and triallylamine for water-solubly crosslinked polymers.

Monomers a), b) and c) used for polymerization may each independently be a single one or more than one monomer a), monomer b) and/or monomer c) in admixture, in which case the conjoint proportion of monomers a), b) or c) indicates the proportion of the polymer which is attributable in each case to monomer a), to monomer b) and to monomer c) respectively.

The total amounts of monomer(s) a) plus monomer(s) b) plus monomer(s) c) always sum to 100 weight percent.

The proportions in weight percent of the total mass of the polymer which are attributable to monomers a) are typically at least 20, preferably at least 30, more preferably at least 50, even more preferably at least 60 weight percent and especially up to 100 weight percent as for example in the case of homopolymers of 100% of a monomer a).

The proportions in weight percent of the total mass of the polymer which are attributable to monomers b) are typically up to 80, preferably up to 70, more preferably up to 50, even more preferably up to 40 and especially less than 5 weight percent and are for example not even present in the polymer.

When the polymer is a crosslinked polymer, the proportions in weight percent of the total mass of the polymer which are attributable to the crosslinking monomers c) are typically from 0.001 to 20, preferably from 0.01 to 10, more preferably from 0.05 to 5 and especially from 0.1 to 3 weight percent such as 0.2, 0.3, 0.4, 0.5, 0.7, 1.0, 1.5, 2 or 2.5.

When crosslinking monomer c) is used, the above-specified total proportions of total polymer solids content which are attributable to monomer a) and the above-specified total proportions of total polymer solids content which are attributable to any monomer b) used correspondingly reduce by the total amount of crosslinking monomer c) used.

A vinyllactam polymer may accordingly be a homo- or copolymer comprising N-vinyllactams such as N-vinylpyrrolidone (VP) or their 3-, 4- or 5-methyl-substituted derivatives, N-vinylpiperidone or N-vinylcaprolactam (VCap). Preference is given to N-vinylpyrrolidone, N-vinylcaprolactam or their mixture. N-Vinylpyrrolidone is especially preferred.

Preferred vinyllactam polymers are vinylpyrrolidone polymers such as polyvinylpyrrolidones, vinylpyrrolidone copolymers and vinylpyrrolidone popcorn polymers.

Polymers according to one or more embodiments of the present invention always comprise at least one N-vinyllactam monomer, preferably N-vinylpyrrolidone and/or N-vinylcaprolactam, more preferably N-vinylpyrrolidone and most preferably only N-vinylpyrrolidone as vinyllactam. More particularly, polymers according to one or more embodiments of the present invention consist of just N-vinylpyrrolidone as single monomer.

Preferred polyvinylpyrrolidones are polymers having K values of 1 to 150, preferably K10 to K120, for example K12, K15, K 17, K25, K30, K60, K85, K90, K95, K100, K115 or K120. Particularly preferred PVP homopolymers have a K value of 12 to 95 and more preferably of 15 to 40, especially K 20, K 25, K 30 and K 35.

Preferred vinylpyrrolidone copolymers are linear, uncrosslinked copolymers with N-vinylcaprolactam (VCap), vinyl acetate (VAc), N-vinylimidazole (VI) and/or its derivatives and/or their mixtures.

Particularly preferred copolymers are copolymers of N-vinylpyrrolidone (VP) with vinyl acetate having a weight ratio VP/VAc of 20:80 to 80:20, for example 30:70, 50:50, 60:40, 70:30, with K values of 10 to 150, preferably of 15 to 80 and especially of 20 to 50, for example 25, 30, 35, 40 or 45. Very particularly preferred copolymers of N-vinylpyrrolidone with vinyl acetate have a K value of 25 to 45 and a VP to VAc weight ratio of 55:45 to 70:30 such as 60:40.

Preference is similarly given to copolymers of VP and VCap with K values of 10 to 100, preferably of 12 to 80 and especially of 20 to 70, for example 30, 40, 50, or 60, and also weight ratios of the VP to VCap monomers of 80:20 to 20:80, preferably of 70:30 to 30:70, more preferably of 60:40 to 40:60 and for example even 50:50.

The K value of vinylpyrrolidone copolymers and polyvinylpyrrolidones (Fikentscher K value; see for instance Baler, "Polyvinylpyrrolidone—Excipient for Pharmaceuticals", Springer, 2005, pages 40 to 41) is a measure of the solution viscosity under defined conditions. Hence it is a direct measure of molar mass. When molar mass changes, for example as a result of oxidative processes (as evidenced for instance by an increase in the peroxide content and/or color deepening/yellowing), this leads to molar mass increase (leads to K value increase) or to molar mass decrease (leads to K value decrease) and thus to change in the K value. When molar mass changes, the solution viscosity of a solution having a defined solids content also changes in corresponding fashion.

Preparation of N-vinyllactam polymers by free-radical polymerization is known per se. Free-radical polymerization with crosslinked monomers c) affords branched or crosslinked polymers which are water soluble to water insoluble depending on the degree of crosslinking in that for example they are gel-forming in water. The polymers prepared by popcorn polymerization (usually referred to in English as "proliferous polymerization"), by contrast, are typically insoluble in water and all solvents. Polymerization without crosslinking monomers c), by contrast, typically affords linear, uncrosslinked polymers.

The monomers may be free-radically polymerized according to the customary processing techniques, for example according to the batch polymerization process, wherein the monomer(s) is/are initially charged in solvent, for example water, and the initiator, for example hydrogen peroxide and a copper(II) salt as catalyst, is added at elevated temperature of 30 to 150° C., preferably of 40 to 95° C. The base, usually ammonia, is usually likewise initially charged with the monomer(s), but can also be added incrementally or continuously. The reaction mixture is preferably stirred at the polymerization temperature until the conversion is more than 99.5 wt %. Usually, at the end, an additional amount of initiator is added and often the reaction temperature is also raised. This phase from addition of additional initiator/raising the reaction temperature is typically referred to as "postpolymerization". When the polymerization temperature at the beginning is too low, the reaction will start badly or not at all. When temperatures are too high, polymer discoloration increases.

A semi-batch polymerization process can also be carried out as an alternative to the batch polymerization process. In semi-batch polymerization, some or all monomer is added during the polymerization. Typically, however, a comparatively small proportion of monomer is usually initially charged in the reaction mixture with the remainder being added over a certain period. The period during which the initiator is added is typically longer than the period during which the monomers are added.

A continuous polymerization process is also possible. In the continuous polymerization process, the monomers and the initiator as well as solvent are introduced continuously and typically concurrently into a reaction vessel, for example a so-called stirred tank cascade or a tubular reactor, with the rate of adding monomer, initiator and solvent at the upstream end of the cascade or tube being matched by a corresponding amount of reaction mixture being removed at the downstream end.

The present process is preferably carried out in stirred tanks according to the batch or semi-batch method. In one alternative embodiment, the process is preferably performed as a continuous polymerization in tubular reactors on the microscale. Microscale is to be understood as meaning that the internal diameters of the individual tubular reactors are less than 2 centimeters and preferably less than 1 centimeter.

Semi-batch and batch polymerization, most preferably batch polymerization, especially in customary stirred tanks is particularly preferable for the present process.

The polymerization is typically carried out in a liquid.

"Liquid" in the context of this invention is to be understood as referring to any substance having a melting point of less than 100° C. and therefore in a liquid state at least in a sub-range of the temperature range from zero to 100° C. at atmospheric pressure, or at least liquefying in such a sub-range as a result of pressure elevation above atmospheric pressure (ambient pressure). Liquids within the meaning of this invention are accordingly organic and inorganic substances such as organic solvents, inorganic and organic salts and also gases. A liquid may similarly be a mixture of two or more different liquids. Liquid is to be understood as referring to a liquid which is or substantially inert in the free-radical polymerization of monomers which are in accordance with the present invention. The liquid may be a solvent or dispersant for the polymer. "Substantially inert" here is to be understood as meaning that the secondary components formed from a reaction with the solvent amount to less than 1000 ppm and preferably less than 500 ppm or less of the polymer solids content.

Typical representatives of organic solvents are for instance C1 to C8 alcohols such as methanol, ethanol, n-propanol, isopropanol, n-butanol and structural isomers, glycol, glycerol, diethyl ether. Preference is given to using methanol, ethanol and/or isopropanol, particular preference to ethanol and isopropanol and very particular preference to isopropanol.

Typical representatives of salts are the salts which are liquid under treatment conditions, i.e. "ionic liquids", imidazole-based for instance.

Typical representatives of gases are for example carbon dioxide, dimethyl ether, ethane, propane or butane. Gases have a particular advantage in that they are easily removable after the treatment by reducing the pressure in the reaction space and causing the gas to automatically evaporate and leave the polymer behind in solid form.

Preference is given to using organic solvents, water and mixtures thereof.

Very particular preference is given to the use of predominantly water. "Predominantly" is to be understood as meaning that the proportion of water is at least 60 percent, preferably at least 70 percent, more preferably at least 80 percent and especially at least 90 percent, for example 95, 99.9 or even up to 100 percent.

Water can be water of differing quality: water of technical grade quality, water of naturally occurring quality such as surface water, river water and groundwater, and also purified water. Purified ("pure") water can be purified by methods of purification such as simple or repeated distillation, demineralization, diffusion, adsorption, using ion exchangers and also activated carbon and other absorbents, using a filtration method such as ultrafiltration and dialysis. "Pure" water herein is typically singly or multiply distilled water and also completely ion-free water.

Preparation according to one or more embodiments of the present invention in the case of soluble polymers is preferably in solution, preferably in aqueous solution and more preferably in pure water in the case of water-soluble polymers. In the case of insoluble polymers, preparation preferably takes the form of precipitation polymerization in water, preferably in pure water.

These methods of preparation are known to a person skilled in the art.

The usual initiators for a free-radical solution polymerization which form free radicals and are known to a person skilled in the art are useful as initiator for the free-radical solution polymerization of vinyllactams such as N-vinylpyrrolidone in particular.

Preferred polymerization initiators comprise all initiators known to a person skilled in the art for the free-radical polymerization of vinyl monomers, especially vinyllactams, such as water-soluble and water-insoluble, preferably water-soluble, peroxides and hydrogenperoxides, and also azo compounds, such as hydrogen peroxide, tert-butyl hydroperoxide, tert-amyl hydroperoxide, cumene hydroperoxide, pinane hydroperoxide, peroxodisulfuric acid and its salts, especially its alkali metal or ammonium salts, and also percarbonates and peroxoesters. Also possible are redox initiators, for example metals with peroxides, (hydro)peroxides with reducing agents such as ascorbic acid, sulfites and the like, and also all initiators disclosed in U.S. Pat. No. 5,262,171. Further known azo initiators are azobisisobutyronitrile and derivatives thereof, for instance the substances known from WAKO as "V50", "V 59" and "V 601". Preference is given to using hydrogen peroxide, tert-butyl hydroperoxide and di-tert-butyl peroxide, for the comparatively low molecular weight polymers in particular. The comparatively high molecular weight polymers preferably utilize especially azo initiators, such as said V59 and V601. Hydrogen peroxide is particularly preferable as initiator, especially for polymerization of N-vinylpyrrolidone as single monomer and especially for K values between 15 and 40.

The initiator is used in amounts of 0.01 to 10 weight percent, preferably 0.05 to 5 weight percent, more preferably of 0.1 to 3 weight percent and even more preferably of 0.2 to 1 weight percent, based on the amount of monomers.

The hitherto customarily used processes for polymerization using hydrogen peroxide in aqueous solutions, usually in water as sole solvent, are known to have several issues:

A—postulated—decomposition mechanism from vinyllactam, especially vinylpyrrolidone, and hydrogen peroxide generates formic acid as one of its end products, and it makes the pH decrease during the polymerization. As a result, starting at a pH of below 5.5 or thereabouts, a slow hydrolysis of the vinyllactam, especially the vinylpyrrolidone, ensues and gets faster and faster at decreasing pH. This generates the free lactam (2-pyrrolidone in the case of vinylpyrrolidone). In fact, such a hydrolysis is observed with the formation of significant amounts of free lactam at up to 5 weight percent in the polymer.

To compensate this, adding a base during the polymerization was started way back in the 1940s to compensate the formation of formic acid Ammonia has become established as the base, inter alia because of its low costs and because of its ease of removal due to thermal volatility. On the other hand, hydrazine, which is toxic, is generated when ammonia is used and process operation is nonoptimal. Polymer obtained in this way is virtually unsellable.

This was compensated via improved process operation and the use of catalysts which made the decomposition of hydrogen peroxide better controllable. The use of copper(II) salts such as cupric dichloride and copper sulfate has become established. Copper(II) combines with ammonia in water to form a blue amine complex. This forms in situ during the reaction or else can also be used as such from the start.

To suppress formic acid formation and hence the hydrolysis of acid-labile monomers to be polymerized, such as the vinyllactams, in a batch or semi-batch polymerization, it is advantageous according to one or more embodiments of the present invention to add the initiator quantity to start the polymerization only once at the start and over a brief period:

Adding the initiator, preferably hydrogen peroxide, in step a) can accordingly take the form of a single dose, which is added as quickly as possible to the initial charge in the reaction container, or as feed stream which is added over a period which is short relative to the entire polymerization time and ranges from a few minutes up to not more than 60 minutes, preferably not more than 45 minutes and more preferably not more than 30 minutes such as, for example, 10, 15 or 20 minutes.

The polymerization then ends leaving a remainder of N-vinylpyrrolidone—frequently of less than 10, but usually of more than 50 ppm although rarely up to 2000 ppm—which should be further reduced because of the toxic properties.

This remainder is then reduced in step e) according to one or more embodiments of the present invention by the action of a sulfur component.

The sulfur component treatment step e) according to one or more embodiments of the present invention is carried out following the polymerization a)/b). The polymerization can but need not comprise a postpolymerization c). When postpolymerization is implemented, step e) according to one or more embodiments of the present invention takes place after said postpolymerization c). Where a polymerization is carried out in an organic solvent or in a mixture of organic solvent and water, it may be advisable first to exchange all or at least some of the organic solvent for water (step d) according to one or more embodiments of the present invention) and then to conduct the treatment (step e)).

When the organic solvent is to be first wholly or partly removed using thermal distillation, the treatment in step e) preferably takes place after such a thermal distillation.

When a steam distillation is provided, for instance to partly, wholly, almost wholly or at least predominantly exchange the organic solvent for water, said treatment e) according to one or more embodiments of the present invention is preferably only carried out after this steam distillation.

When both a thermal distillation and a subsequent steam distillation are provided, the treatment according to one or more embodiments of the present invention takes place before or after the steam distillation, preferably after the thermal distillation and more preferably only after the steam distillation.

When, accordingly, purification by stripping with gas, thermal distillation and/or steam distillation is provided (step d)), then step e) is carried out after this step d) in particular.

The polymer solutions or dispersions to be treated using step e) typically have a solids content of 5 to 80 wt % and preferably of 5 to 60 wt %. In dispersions, the solids content is more preferably in the range from 5 to 25 wt % and especially in the range from 8 to 15 wt %. The solutions or dispersions used can be as-obtained directly from the polymer synthesis, for instance in the polymerization or postpolymerization solvent or the solutions or dispersions thereof following complete or partial solvent exchange, for instance by thermal distillation or steam distillation. But it is also possible in principle for solid polymers to be dissolved or dispersed and then treated according to one or more embodiments of the present invention.

The treatment according to one or more embodiments of the present invention is preferably carried out in aqueous solutions or in aqueous dispersions. These aqueous solutions or dispersions are more preferably obtained directly from the polymerization (step a/b), the optional postpolymerization c) following the polymerization, or the step d) purification following the polymerization with or without the postpolymerization, and used.

The solids content of the solutions and dispersions to be treated may, if desired, for instance for better commixing, be reduced by adding a suitable solvent. The solids concentration can be increased by removing solvent, for instance by thermal distillation.

Following this step e) sulfur component treatment according to one or more embodiments of the present invention, the polymer solution may optionally pass through a renewed purifying step d), for example by stripping with for instance steam in order that for example excess sulfur component, especially sulfur dioxide, may be removed. Such steam stripping is preferably performed after step e).

The preferred embodiments 1 to 84 of the present invention are therefore preferably embodied by the treatment with sulfur component, especially with sulfur dioxide, being followed by excess sulfur component such as sulfur dioxide being removed from the reaction mixture by stripping, especially with steam.

"Excess" is to be understood as meaning that amounts of sulfur component, preferably sulfur dioxide, are removed until the amounts remaining in the polymer are those which are described as preferred in this invention. The amounts of salts of sulfurous acid are equimolar to the sulfur dioxide.

In the embodiments of the present invention such as more particularly the preferred embodiments 1 to 84, the purification in the renewed step d) following step e) commences with stripping, preferably with steam, more preferably immediately after the sulfur component has been added or with a time delay of up to four hours, preferably up to three hours, more preferably up to two hours, even more preferably up to one hour and especially up to 30 minutes. This stripping, especially with steam, takes from 10 to 150 minutes, preferably from 20 to 120 minutes and more preferably from 30 to 90 minutes, for example 45, 60 or 75 minutes.

Stripping time influences the odor properties of polymers obtained. Particularly good, i.e., neutral, odor is achieved in the course of about 60 minutes. But even 30 minutes can suffice if a slight intrinsic odor on the part of the polymers can be tolerated in the intended use.

Batch size dictates the actual stripping time needed. The recited values hold for batches as exemplified, of up to several 100 kilograms. The time needed in any one case is easily ascertained by a person skilled in the art from individual tests shown, and particulars provided, in the context of this invention.

Step e) according to one or more embodiments of the present invention and optional renewed purification d) by for instance stripping after step e) may be followed by a step f) of adding a base to set a desired pH higher than that during step e).

Any base which a person skilled in the art considers suitable for adjusting polymer solutions is suitable. They include for example all secondary amines (for instance those disclosed in paragraph [0036] of EP 1950230 A1, which are hereby fully incorporated herein by reference), tertiary amines and also primary, secondary and tertiary alkanolamines, dialkanolamines and trialkanolamines, wherein all amines each preferably have only C1 to C6-alkyl chains which may bear one or more alcohol groups, such as monoethanolamine, diethanolamine, triethanolamine, 2-amino-2-methyl-1-propanol, 2-amino-1-butanol, tris(hydroxymethyl)-aminomethane, 2-amino-2-ethyl-1,3-propanediol, 2-amino-2-methyl-1,3-propanediol or triethylamine. Also suitable are for example ammonia and basic ammonium salts, basic carbonates such as ammonium, sodium and potassium carbonate and hydrogencarbonate, sodium and potassium hydroxide and their specifically aqueous solutions, guanidine and its derivatives and salts such as guanidine carbonate.

Preference is given to using ammonia, diethanolamine, triethanolamine, 2-amino-2-methyl-1-propanol, 2-amino-1-butanol, tris(hydroxymethyl)aminomethane, 2-amino-2-ethyl-1,3-propanediol, 2-amino-2-methyl-1,3-propanediol, triethylamine, ammonium hydroxide, sodium hydroxide, potassium hydroxide, ammonium (hydrogen)carbonate, sodium (hydrogen)carbonate and potassium (hydrogen)carbonate. Particular preference is given to ammonia, diethanolamine, triethanolamine, 2-amino-2-methyl-1-propanol, tris(hydroxymethyl)aminomethane, triethylamine, ammonium carbonate and ammonium hydrogencarbonate. Ammonia, triethanolamine 2-amino-2-methyl-1-propanol, tris(hydroxymethyl)aminomethane and triethylamine are very particularly preferred.

It is especially preferred to use ammonia as base in step f), especially in embodiments 2 to 84 in which step f) is implemented.

It is likewise especially preferred to use 2-amino-2-methyl-1-propanol (AMP 95) as base in step f), especially in embodiments 2 to 84 in which step f) is implemented.

Step e) according to one or more embodiments of the present invention and the optional addition of a base to adjust the pH (step f)) may be followed by purifying the resulting polymeric solution using filtration (step g)).

The polymer solution can be freed of or depleted in ingredients using filtering methods and filter media known to a person skilled in the art. Physical methods of filtering and chemical methods of filtering are suitable. Specifically mechanical filters such as sieve, mesh and nonwoven filters are suitable for removing solids by selected average pore size and pore size distribution. Chemical filters are specifically ion exchangers and adsorbents which remove metal ions or organic ingredients for example by complexation and/or reaction with the filter medium. Also conceivable are physical filters such as the adsorption of ingredients on activated carbon for example. Filtration using osmosis, reverse osmosis, ultra and dialysis membranes is also conceivable. Preference among all these methods is given to filtration through mechanical filters, filtration via adsorption and filtration using membrane filters. Particular preference is given to filtration via adsorption and using mechanical filters, especially using mechanical filters. Purifying preferably conditions the polymer obtained according to one or more embodiments of the present invention such that fractions in the polymer which are sparingly soluble or less soluble than "sparingly soluble" (solubility definition as per DAB 10, German Pharmacopeia Edition 10, as quoted in Roempp for example) are removed from the polymer such that their proportion amounts to less than 500 ppm, preferably less than 150 ppm, more preferably less than 100 ppm, even more preferably less than 70 ppm and especially less than 50 ppm per kg of polymer based on the polymer solids content. These quantitative particulars relate to a filter having an average pore size of 5 micrometers, preferably 2 micrometers, and a narrow pore size distribution which corresponds for example to a Gaussian distribution or, preferably, is 10 percent, preferably 20 percent, narrower than a Gaussian distribution.

The sparingly soluble or insoluble fraction is customarily referred to as "gel content". A polymer would accordingly have a "gel content of less than 70 ppm" for example when the amount of removables is less than 70 ppm (based on the stated pore size, filter medium and filtering conditions).

Suitable methods of measurement are known to a person skilled in the art, for example from EP 1 950 230 A1, the disclosure of which regarding filtration residue and its determination is hereby fully incorporated herein by reference.

When a drying step h) is implemented, step e) according to one or more embodiments of the present invention preferably takes place before the drying step. But it is also possible in principle to subject redissolved or redispersed polymeric powder to step e) of the present invention. When redissolved/redispersed polymer is subjected to step e), the further steps d), f), g) and h) can likewise be redeployed, if desired.

Any drying method known to a person skilled in the art is suitable in principle, such as drying by spraying in air or a gas (such as spray drying, including via spray disks and so-called jetbrooms, fluidized-bed spray drying, spray agglomeration and pneumatic-conveyor drying), drying on contact surfaces (such as drum drying, belt drying and paddle drying) and drying via vacuum such as freeze drying and freeze concentrating or drying via radiation such as microwaves.

Drum drying can in principle utilize any drum dryer known to a person skilled in the art, for instance a drum dryer having one or two main rolls and none to six, preferably two to five, about three or four secondary rolls, more preferably four or five, especially five secondary rolls. These secondary or satellite rolls typically have a distinctly smaller diameter than the main roll.

Satellite rolls function inter alia as applicator roll(s) and as secondary roll(s) to compress the polymer layer on the main roll. Satellite rolls can in principle be arranged in any desired manner. Suitable arrangements are known to a person skilled in the art. Suitable optimizations to the polymer solutions to be dried are familiar to a person skilled in the art. Arrangements with typically two to six satellite rolls typically feature overhead satellite rolls, i.e., the small, secondary rolls are positioned in the upper region of the main roll. "Upper region" is to be understood as meaning that the satellite roll axes are arranged above the main roll axis. However, the axis of the last secondary roll especially in the case of three or more satellite rolls can also be arranged between the main roll axis and the lower boundary of the main roll. The first two to three, rarely four secondary rolls combine to form one to three "sumps" into which the polymer solution is metered. Compression and/or multiple application of polymer solution/dispersion to the same place on the main roll in the course of the same revolution (i.e., two or more layers of polymer solution on top of each other) can be used to achieve higher densities for the solid polymeric material obtainable. Sideways sealing for the sumps between the satellite rolls and the main roll is known to a person skilled in the art, for instance in the form of suitable metal plates, sliders, etc.

The arrangement with two counterrotating main rolls which (can) form a sump between the main rolls is also known in principle and implementable in the context of the invention. The arrangement of satellite rolls can follow the same pattern as described for the arrangements with one main roll. Typically, however, such twin roll dryers need fewer satellite rolls per main roll, typically usually only one to three, preferably one or two satellite rolls per main roll. The sumps are formed by two satellite rolls, the two main rolls and combinations thereof. An arrangement that is conceivable but rarely used for polymer solutions is that of one or two applicator rolls (satellite rolls) in the lower region of a single main roll, or the doubling thereof with two main rolls.

The technique of drum drying as such and also the many possible embodiments, the various types and number of applications, the various known and conceivable mechanical, optical, electrical and electronic sensors for instance for fill level height measurement and control of the "sump" or "sumps" are well known to a person skilled in the art, for instance from a sixteen-page brochure "Drum Dryers" of machine makers Royal-GMF Gouda ("Goudsche Machine-fabriek B.V."), Netherlands, dated 1995, especially the drawings therein on pages 4, 5 and 14, from "Drum Drying", J. Tang, H. Feng, G-Q-Shen in "Encyclopedia of Agricultural, Food and Biological Engineering", 2003, Marcel Dekker, in Handbook of Industrial Drying, 2007, CRC/Taylor&Francis and further reference works in the field of chemical engineering, in the field of process engineering and in the field of mechanical engineering.

This invention gives preference to using drum dryers having one applicator roll and four or five, more preferably five overhead satellite rolls and one or two, preferably two sumps for drying polymer solutions, preferably aqueous polymer solutions, of vinyllactam polymers, preferably vinylpyrrolidone polymers, more preferably polyvinylpyrrolidone, having K values of 10 to 150, preferably 50 to 130, more preferably not less than 60, even more preferably not less than 80 such as for example 85, 90, 95, 100, 110 or 120, and more preferably up to 120 and even more preferably up to 100.

Spray drying by spraying into a hot gas or hot air is preferable, especially for polymers having molar masses up to about 200 000 g/mol weight-average molar mass ("comparatively low molecular weight polymers").

Drying on hot contact surfaces such as drum drying is preferable for polymers having higher molar masses than about 200 000 g/mol weight-average molar mass ("comparatively high molecular weight polymers").

However, polymers having molar masses below 200 000 g/mol can also be dried by drying on hot contact surfaces and polymers having molar masses above 200 000 g/mol weight-average molar mass can also be dried by spraying, for instance via spray drying.

A person skilled in the art is very familiar with optimizing the particular polymer solutions or dispersions by optimizing for instance the solids content to the method of drying to be used. Excessively high solution viscosities usually give rise to issues in relation to spraying, and therefore comparatively high molecular weight polymers have to be sprayed in comparatively dilute solutions, while comparatively low molecular weight polymers can still be sprayed at higher solids contents than the comparatively high molecular weight polymers. Similarly, comparatively low molecular weight polymers can be dried at higher solids contents via contact surfaces, for instance drum drying, while excessively low solids contents there can cause issues since the solutions of comparatively low molecular weight polymers are often too liquid on the contact surface and do not generate sufficiently thick layers there. A possible issue arising therefrom is for instance an excessively low density (and hence an excessively large packing volume per kilogram of polymer), an excessively low space-time yield and excessively high costs for manufacture and packaging.

One particular advantage of the present process is that the polymerization is carried out at high concentrations of monomer and therefore polymer solutions having high concentrations of solids are obtainable. Process performance is preferable at monomer concentrations of not less than 30 weight percent, more preferably not less than 35 weight percent and even more preferably not less than 40 weight percent and especially not less than 45 weight percent such as 50 or even 55 weight percent in the production of vinyllactam polymers, especially PVP, having K values of 10 to 50, preferably 20 to 40 and more preferably 25 to 35. Customary issues such as excessively high viscosities, which compromise stirring and hence commixing of the reaction batch, only arise to a very much smaller degree than in existing processes, if at all. It will be appreciated that the polymerization can also be carried out at lower solids contents below 30 weight percent, for instance 25, 20, 15 or only 10 weight percent, in which case the economic advantages due to the higher concentration are then correspondingly lower.

The lower the K value of the polymer to be produced, the higher the solids concentration can be. This relationship is well known to a person skilled in the art. Therefore, optimizing the present process according to the invention regarding the solids contents to the desired K values can be done by a person skilled in the art easily and without exercising inventive skill. For K values of 25 to 35, especially for PVP, solids contents of 30 to 50, preferably of 35 to 45 weight percent for example are easily realizable with the present process without having to compromise desired polymeric properties or accept disadvantageous processing parameters.

A further particular advantage of the present process is that the polymerization succeeds with short reaction times without having to adopt the otherwise customary approaches such as very high initiator concentrations and/or high temperatures. Familiar issues due to measures of this type such as yellowing, gel particle formation and broad molar mass distributions (often due to departures from the linearity of polymer chains in the case of uncrosslinked polymers, possible causes for the departures being unwanted secondary reactions such as linking of polymer chains or contamination with crosslinking monomers), high proportions of secondary components and/or unwanted decomposition products such as formic acid, formate and lactam contents such as pyrrolidone contents for instance are avoided using the present process.

The reaction times needed in the context of the production process according to one or more embodiments of the present invention are typically less than 6 hours for the polymerization, preferably less than 5 hours, more preferably less than 4 hours and even more preferably less than 3 hours such as, for example, 2 hours or less even in the case of reaction batches of more than one metric ton.

The production process of one or more embodiments of the present invention thereby provides high space-time yields of polymers of very good quality which for example have lower values in respect of color, odor, viscosity, cloudiness and gel content than previously known polymers. More particularly, the polymers obtainable according to one or more embodiments of the present invention, especially polymers obtainable according to the preferred embodiments 1 to 84, have values in respect of color, odor, viscosity, cloudiness and gel content that remain more consistent in storage than is the case with the previously known polymers. More particularly, color and odor are particularly low compared with prior art polymers.

The present process can further be carried out at various pressures. The polymerization can be carried out under reduced pressure, atmospheric pressure (ambient pressure) as well as under superatmospheric pressure. In principle, all pressure ranges are possible in that limitation is essentially imposed by technical feasibility and/or the necessary costs.

Superatmospheric pressure is typically limited by the pressure resistance of reactors for conducting the reaction and/or the costs for such high pressure resistant reactors.

Reduced pressure is typically limited by the temperature at which polymerization is then still possible, since reducing the pressure will cause the solvent, for instance water, to start to boil even at lower temperatures and therefore the initiators have to be chosen such that they have corresponding low disintegration times to still form sufficient free radicals at the low polymerization temperatures. But initiators having such low disintegration times are a safety issue due to their instability in storage and therefore are generally undesirable.

As will be known to a person skilled in the art, the solids content of monomers in a polymerization under pressure and hence the solids content of polymers in solution in the reactor is also dependent on the maximum pressure rating of the reactor vessel owing to safety-engineering limitations in the design of pressure reactors for free-radical polymerizations of olefinically unsaturated monomers such as vinyllactams, for example vinylpyrrolidone. The higher the allowed pressures, the higher the theoretically possible solids contents. Choosing the solids content and the pressure accordingly also inevitably amounts to choosing a suitable reactor vessel.

As a person skilled in the art will know, when a polymerization is carried out at ambient pressure (that is, in an "open system", in which the reaction space is not sealed off from the atmosphere but merely separated from the atmosphere by, for instance, gas blanketing or a valve which effects closed-loop control of the pressure in the reaction vessel to ambient pressure), the solids content which a polymerization process can accommodate for the monomers in the reactor and hence the polymer solids content which is attainable is dependent on the cooling performance of the cooling system with which the reactor is equipped. The cooling system for a polymerization in an open system has to be able to ensure the safety of the system, i.e. be capable for example of checking sudden severe boiling due to a sudden severe heat of polymerization. The design of the cooling system—together with the viscosity of the polymer solution obtainable—accordingly limits the maximum possible solids content in polymerizations carried out in open systems.

These essentially practically based limitations result in a pressure range of 30 000 pascals up to 5 million pascals as a technically sensible range for polymerizations.

The pressure range in which the present process is accordingly carried out is preferably from 30 000 pascals up to 5 million pascals, more preferably from 80 000 to 2 million pascals, more preferably from 90 000 to 1.5 million pascals, even more preferably not more than 1 million pascals and especially not more than 800 000 pascals, for example 600 000, 400 000 or 200 000 pascals. Polymerization at ambient pressure in an open system as described above is most preferable.

Particularly advantageous results in respect of coloration were surprisingly obtained on polymerizing at ambient pressure. The polymers obtained have the lowest yellowing, are colorless or almost colorless and are more particularly completely colorless even at concentrations of 30 to 45 weight percent in aqueous solution. Color indications for polymer contents in aqueous solution are reported as indicated in each case. Solids contents relate to the values without dilution, i.e., as-polymerized, unless a particular solids concentration is reported. The color indication determined using the eye of a practiced expert are correlated with the Hazen color number measurement:

"colorless"=Hazen below 20; "almost colorless": Hazen 20 to 30; "minimally yellowish"=Hazen above 30 and below 40; "yellowish"=Hazen 40 and below 60; "yellow"=Hazen 60 or above.

These color indications correlate Hazen measurements with the color perception in words which the human eye detects on looking through an aqueous solution of polymers for a path length of 5 centimeters (in a colorless vessel made of glass). It must be noted that slight turbidity—which need not be visible to the human eye since for instance colloidal turbidity is due to particles in the submicron range (a "solution" ought then to be more correctly referred to as "suspension")—will distort the measured result to the effect that significantly higher Hazen values are measured, these significantly higher Hazen values corresponding to a massive yellow or even brown coloration, while the solution is nonetheless colorless or almost colorless to the human eye. Since color as perceived by the human eye is the relevant variable in relation to using such polymers, therefore, the color reported in words is deemed to be the relevant variable in the context of this invention. The measured values provide support. Individual departures of the Hazen color number in the upward direction, even though the color as perceived by the human eye is significantly less than it is to judge by the Hazen value, are evidence of turbidity which is usually not visible to humans.

However, a particular advantage of the present process is that not only the color as perceived by the human eye but also the measured Hazen values are generally very low. This means that not only the coloration but also the turbidity due to colloidally dispersed solids (such as gel particles) in embodiments A1, A2 and 1 to 84 of the present invention and more particularly in the preferred and the more preferred embodiments are particularly low.

However, a polymerization at superatmospheric pressure in the present process is capable of providing solids contents up to 60 weight percent, preferably up to 55 weight percent and more preferably up to 50 weight percent at pressures of preferably up to 1.6 million pascals, more preferably up to 1 million pascals and even more preferably up to 800 000 pascals.

The higher the pressure, however, the greater the coloration of the polymer, and therefore the present process is most preferably performed at ambient pressure.

The pH measured at the start and the end of the polymerization varies with the type and amount of base added in step b).

Depending on the initiator used and the type and amount of base added, the pH decreases in the course of the reaction and can have values down to about 4. This reduction is more particularly observed when hydrogen peroxide is used as initiator. The end of polymerization is accordingly already the start of residual-monomer hydrolysis, since acidic hydrolysis of vinyllactams starts at below about pH 5.5. If the pH at the end of polymerization is likewise still to be above 5.5 or—preferably—6 in order that any acidic hydrolysis at the end may be foreclosed and in order that acidic hydrolysis—if desired—may be started in controlled fashion, the amount of base must be increased. A person skilled in the art is very easily able to determine suitable quantities for the base used by performing individual tests.

The polymerization in step a)/b) is preferably performed according to one or more embodiments of the present invention at a pH in the range from 5 to 11, preferably not less than 5.5, more preferably not less than 6 and even more preferably not less than 6.5, for example 7, 7.5, 8, 8.5, 9 or 9.5, in order that any hydrolysis of N-vinylpyrrolidone may be avoided. It is particularly preferable for the pH at the start of the polymerization to be not less than 8, even more preferably not less than 9 and especially not less than 9.5 such as 10, 10.5 or 11. Setting a high initial pH ensures that the pH does not decrease so much in the course of the polymerization, especially when hydrogen peroxide is used as initiator. In addition, the choice of base type and amount can be used to control the pH decrease. It is preferable according to one or more embodiments of the present invention, especially in embodiments 1 to 84 of the present invention, for the polymerization to take place at high initial pH values of not less than 9, preferably not less than 10 such as for example 10.5 or 11, and with such bases and base quantities that the final pH of the polymerization does not drop below pH 5.5 and preferably not below pH 6.

Appropriate adjustments are directly accessible to a person skilled in the art by performing individual tests on the basis of the examples shown.

It is therefore preferable for the solutions of the individual components to be adjusted to this pH before commencing the polymerization as per step b) using a base (the same substances are selected as bases as indicated for step f)), preferably aqueous sodium hydroxide solution, sodium hydrogencarbonate, aqueous ammonia solution, 2-amino-2-methyl-1-propanol, tris(hydroxymethyl)aminomethane or else ammonium hydrogencarbonate or carbonate, by single addition or via a brief feed stream as described above. No further bases are added during the polymerization.

Alternatively and less preferably, the pH of the reaction medium is kept in the range from 5 to 10 during the polymerization by adding such a base, preferably sodium carbonate or hydrogencarbonate, aqueous ammonia solution, ammonium hydrogencarbonate or ammonium carbonate, more preferably ammonium hydrogencarbonate or carbonate. Maintaining the pH during the polymerization can be done by careful addition of particular amounts—by prior simple trial and error in one or two tests for instance—of base or by continuous or repeated, multiple determination of the pH during the reaction and then appropriate addition of base to reset the desired pH. Both embodiments provide the same result within the margin of error.

The advantage of adding base once is the simplified reaction control and the elimination of the need for continuous pH determination and hence also the elimination of the need for the controlled addition of base. This makes the monitoring of two processing parameters redundant, which amounts to a cost saving and minimizes sources of error.

In one preferred embodiment, the base, more preferably ammonium hydrogencarbonate, ammonia and 2-amino-2-methyl-1-propanol, is added at the start of the polymerization in step a)/b). This means that the base is already added at the start of the polymerization reaction, preferably as single dose, which is added as quickly as possible to the initial charge in the reaction vessel, or as feed stream which is metered over a period which is relatively short in relation to the overall polymerization time, of a few minutes up to not more than 60 minutes, preferably not more than 45 minutes, more preferably not more than 30 minutes such as, for example, 10, 15 or 20 minutes.

Preferably there is no further addition of base during the polymerization.

It is particularly preferable in the context of the present invention, especially in the preferred embodiments 1 to 84, for the pH in step b) to be adjusted at the start by addition of base and for no further base to be added during the polymerization. It is especially preferable here for ammonium hydrogencarbonate to be used each time as base in step b).

The typically desired low residual monomer contents of less than 100 ppm are achievable according to prior art publications and according to common general knowledge in the art via an optional postpolymerization where further initiator, preferably the same one as also used for the polymerization, is freshly added. The addition of further initiator can in turn take the form of a single dose, a metered addition or repeated dosing or repeated metering or combinations thereof. Typically, the (metered) addition of two, preferably only one further portion(s) of initiator is sufficient to lower the residual monomers, especially in the case of vinyllactams such as vinylpyrrolidone, to values of not more than 200 ppm, preferably not more than 100 ppm, more preferably not more than 50 ppm such as for instance less than 10 ppm based on the polymer solids content. However, the postpolymerization time needed to achieve such low residual monomers is generally not allowed to run its course, since reactor occupancy time is too expensive.

Therefore, it is prior art to generally perform such a postpolymerization for a shorter period than actually necessary. The reduction in residual monomers which is then still necessary is achieved, according to prior art publications, via other processing steps, for instance the acidic hydrolysis of the monomers.

Surprisingly, practicing the present process without further addition of initiator and hence without postpolymerization (step c)) results in residual levels of monomers, especially in the case of vinyllactams such as vinylpyrrolidone, which are so low that postpolymerization is not needed, since the values are already so low without such postpolymerization (step c)) that the remaining reduction is reduced by the sulfur component addition step e) of the present invention to such values of not more than 100 ppm, preferably not more than 50 ppm, more preferably not more than 10 ppm, even more preferably not more than 5 ppm and especially not more than 1 ppm based on the polymer solids content.

This abandonment of the further addition of initiator and hence the abandonment of step c) is advantageous particularly because it transpired that the addition of further initiator also leads to a color intensification or any coloration of the polymers in the first place. In addition, the processing time needed and hence the reactor occupancy time can be reduced, which represents a further saving.

It is therefore particularly preferable in the context of this invention to proceed with only one addition of initiator at the start of the polymerization reaction in step a) and to do without step c). Of embodiments 1 to 84 of the present invention, therefore, those embodiments are preferred which are carried out without the subsequent addition of further initiator and hence without step c).

It was accordingly obvious to destroy the remaining, albeit low but nonetheless undesired, residual vinylpyrrolidone content via an acid treatment in accordance with the prior art publications instead of via initiator addition. Typically, the polymer solution is adjusted to a pH of less than 4 with an organic or inorganic acid. This hydrolyzes the vinylpyrrolidone in the aqueous medium into acetaldehyde and pyrrolidone as described for instance in Kirk-Othmer (section "N-Vinylamide polymers" in "Encyclopedia of Polymer Science and Technology", 2005, John Wiley & Sons, Inc).

This acid treatment stops any further formic acid being formed subsequently. The acetaldehyde formed can subsequently be removed via a gas stream e.g. nitrogen, partial removal by distillation, or via steam stripping. But this process has the disadvantage that using various inorganic and organic acids typically used in the prior art—such as sulfuric acid, phosphoric acid, hydrochloric acid, formic acid, lactic acid, produces an undesired deep yellow discoloration of the solution.

The step e) sulfur component use according to one or more embodiments of the present invention, preferably sulfur dioxide as aqueous solution, has the effect that this discoloration during hydrolysis is no longer observed. A colorless or almost colorless polymer solution or dispersion is obtained. The polymer solution or dispersion obtained remains unchanged or almost unchanged in color terms for several months even at a storage temperature of room temperature (25° C.) or 40° C. or even higher and also at comparatively high moisture contents or combinations of these temperatures and humidity values. Even a somewhat higher stability in the presence of atmospheric oxygen was observed, which is why oxygen-caused discolorations and other deteriorations for instance in the viscosity of polymer solutions, the odor and clarity occur distinctly less. Similarly, superior performance characteristics and a higher stability of these characteristics are obtained, for instance in hair gels and hair-cosmetic formulations.

Sulfurous acid (sulfur dioxide as aqueous solution) was never given any consideration in the prior art as a useful acid for acidic hydrolysis. The sole known use is to add sulfurous acid for stabilization. But this addition takes place in the above-cited document DE 10 2005 00 5974 at neutral pH values, at least however at pH values above 6 and hence outside the pH ranges in which hydrolysis of vinyllactam monomers, especially vinylpyrrolidone, can be observed. Adding sulfur dioxide or sulfites as described in GB 836,831 to reduce/prevent yellowing in the course of heating polymer solutions is likewise not a prior description of step e) according to one or more embodiments of the present invention, since the sulfur compounds are added therein to final polymers at a fixed quantitative ratio to the polymer. As a result, the tests therein do not reduce the pH below 5.5 and hence do not achieve any acidic hydrolysis. On the contrary, the amounts used therein have the effect that an aqueous PVP solution having a pH of 8 only decreases minimally to a pH of 7.7. The acidic pH is not solely achieved by adding a sulfur compound in amounts disclosed therein. The sole purpose of the sulfur compound in GB 836,831 is therefore, as disclosed therein as core of the invention there, as a stabilizer in heating, but not as an acid for acidic hydrolysis.

The use of sulfur dioxide in aqueous solution as an acid for hydrolysis was accordingly unknown. The discovery of unexpected properties resulting from the previously unknown use of sulfur dioxide as an acid for such an acidic hydrolysis is one advantage of one or more embodiments of the present invention.

The process of one or more embodiments of the present invention and more particularly the preferred embodiments 1 to 84 are therefore carried out by a postpolymerization time (without initiator addition) of 10 minutes to 4 hours, preferably 30 to 60 minutes, and the optional, but preferably implemented purification in step d) via preferably steam stripping being followed by the polymer solution in step e) of the present invention being adjusted to a pH of less than 4 with sulfur component in aqueous solution, preferably sulfur dioxide in water, and stirred at between 40 and 150° C., preferably 50 and 90° C. This reduces the residual monomers to such an extent that they are at not more than 100 ppm, preferably not more than 50 ppm, more preferably not more than 10 ppm, even more preferably not more than 5 ppm and especially not more than 1 ppm based on the polymer solids content. The polymers obtained have an extraordinarily low color and are colorless or almost colorless and generally have further advantageous properties as described in the context of this invention.

This is achieved according to one or more embodiments of the present invention by treatment with sulfur component without, however, contaminating the polymer with other substances such as enzymes, metals, heavy metals or antioxidants, as proposed in the prior art. The sole additional ingredient is sulfur dioxide, its sulfite salt or its oxidative descendent products, sulfate and hydrogensulfate. The preferred use of sulfur dioxide instead of sulfites also does not introduce any metal ions such as sodium, potassium, magnesium or calcium whatsoever. As a result, the ash content of the polymers also does not increase or at least not as much as if metal salts had been introduced.

The ash content is determined as "sulfate ash content" by the ash content determination known to a person skilled in the art. The ash content is preferably not more than 0.05 weight percent, more preferably not more than 0.02 weight percent, more preferably not more than 0.01 weight percent and even more preferably not more than 0.005 weight percent such as for example merely 0.002 weight percent, 0.001 weight percent or less.

Such low ash contents of not more than 0.02 weight percent or less are obtained especially when the base used in step b) and/or in step f) is one or more substances which do not contribute to the ash content and/or are easy to remove residuelessly or almost residuelessly via simple processing operations such as distilling, stripping or degassing at comparatively high temperature or by applying a vacuum. The recited ash content relates to the overall mass of polymer obtainable according to one or more embodiments of the present invention, based on the solids content of polymer.

Particular preference for use as base in step b) and step f) is therefore given to 2-amino-2-methyl-1-propanol (AMP 95), ammonia, ammonium hydrogencarbonate and ammonium carbonate Ammonium hydrogencarbonate and ammonium carbonate, especially ammonium hydrogencarbonate, are very particularly preferred for step b). Ammonia and 2-amino-2-methyl-1-propanol (AMP 95) are very particularly preferred for step f).

One particular advantage of the present process and of embodiments 1 to 84 disclosed herein and of polymers obtainable therefrom is the comparatively high pH of polymer solutions, so less base is needed to set comparatively high pH values for neutralization for instance. This is advantageous especially because formulations, for instance hair-cosmetic formulations, for example hair gels, have to be admixed with less base. This reduces the salt load borne by such formulations. This cuts costs and affords the formulations greater flexibility due to fewer and less by way of ingredients.

It was also observed in the context of the present invention that hair gels, especially clear hair gels having a carbomer-type thickener content, comprising the polymers obtainable according to one or more embodiments of the present invention have a comparatively high gel stability.

Even after a stripping operation, the polymer solution will typically still contain residual amounts of sulfur component which are further reducible via a further, optional aftertreatment with peroxides such as the addition of hydrogen peroxide.

For color stability, however, it is more particularly advantageous—and accordingly a preferred embodiment or among embodiments 1 to 84 in particular—when the polymer still contains certain amounts of sulfur dioxide/sulfite which equal not less than 10 ppm, preferably not less than 100 ppm, more preferably not less than 200 ppm and even more preferably not less than 500 ppm such as, in particular, 1000 ppm based on the polymer solids content, such as 300, 400, 600, 700, 800, 900, 1100, 1200, 1300, 1400, 1500 or even 1750 ppm.

It is further advantageous when the amounts of sulfur dioxide/sulfite do not exceed a value of 5000 ppm, preferably 3000 and more preferably 2000.

The quantitative recitations are all based on "sulfur dioxide" or, in the case of sulfites, on sulfur dioxide equivalents (i.e., reckoned as "sulfur dioxide").

The polymers obtainable according to one or more embodiments of the present invention have the following characteristics:

The polymers are colorless, almost colorless or minimally yellowish. This is especially the case even with PVP homopolymers having K values of 20 to 40. This low coloration ("almost colorless") or colorlessness ("colorless") is more particularly also present in the polymer solids concentrations of 20 to 60 weight percent in water which are commercially customary at these K values.

The color is indicated as HAZEN color number (also called platinum-cobalt color number and described in DIN ISO 6271-1). The indications concerning color via determination using a practiced eye and correlation thereof with Hazen color values were already discussed above.

The color determined using the practiced eye counts. The Hazen color number value is merely a supplementary indication. If this Hazen color number value is also low, the solution is accordingly also clear without or—in the case of minimally elevated Hazen color number values but colorlessness determined using the eye—almost without turbidity.

The polymers obtainable according to one or more embodiments of the present invention are accordingly minimally yellowish, colorless or almost colorless, preferably colorless or almost colorless and more preferably colorless, all determined by the practiced eye of a person skilled in the art, determined on aqueous polymer solutions in a path length of 5 centimeters, preferably at high polymer solids concentrations as-obtained for the polymers from the polymerization and workup, especially that is at the preferred high solids contents as specified above, and especially in the preferred embodiments 1 to 84.

The Hazen color number values accordingly have the values which were directly correlated with these color indications as specified above.

The polymers obtainable according to one or more embodiments of the present invention, especially the polymers obtainable using embodiments 1 to 84, additionally have color stability in storage under the storage conditions and storage and transport packaging as specified in the context of this invention. This stability is characterized in that the color indications show no or virtually no deterioration in color on storage for a period of 4 weeks, preferably 8 weeks, more preferably 3 months, even more preferably 5 months and especially 1 year or even 2 to 3 years at room temperature and also at elevated temperatures of 40° C. or even 50° C. in the packages mentioned.

"Almost no" deterioration is to be understood as meaning that the value changes by less than 20 percent, preferably less than 10 percent and more preferably less than 5% of the initial value. More particularly, there is no deterioration in color relevant to the particular use.

The polymers give a clear solution without turbidity in aqueous solution especially. Measurable turbidity is very low, preferably below 3, preferably below 2.5, more preferably below 2, even more preferably below 1.5 and especially below 1, such as 0.9, 0.8, 0.7, 0.6, 0.5 or even 0.4, 0.3, 0.2, 0.1 or lower, when determined as FTU value in accordance with DIN ISO 15715 on a 10 weight percent aqueous polymeric solution.

The polymers obtainable according to one or more embodiments of the present invention, especially the polymers obtainable using embodiments 1 to 84, additionally have turbidity stability in storage under the storage conditions and storage and transport packaging as specified in the context of this invention. This stability is characterized in that the turbidity indications show no or virtually no deterioration in turbidity on storage for a period of 4 weeks, preferably 8 weeks, more preferably 3 months, even more preferably 5 months and especially 1 year or even 2 to 3 years at room temperature and also at elevated temperatures of 40° C. or even 50° C. in the packages mentioned.

The polymers display only little if any technically relevant, preferably not even measurably relevant, change in the viscosity of an aqueous solution on storage at room temperature (25° C.), or, preferably also not on storage at elevated temperature of up to 40° C., preferably up to 50° C. Polymers obtainable by the present process display viscosities in their aqueous solutions which are lower compared with polymers obtained using prior art processes. "Lower" here is to be understood as meaning that the viscosities exhibit up to 5 percent, preferably more than 5 percent, more preferably more than 7 percent and more preferably more than 10 percent lower viscosities than polymers of the prior art under otherwise identical conditions of measurement. Polymers obtainable by the present process exhibit a stable viscosity in storage in that the viscosity of the aqueous solution following a storage time of at least 3 months, preferably at least 6 months, more preferably at least 9 months, even more preferably at least 12 months and especially at least 2 years has a viscosity change of not more than 15%, preferably not more than 10 percent, more preferably not more than 5%, even more preferably not more than 3 percent and especially not more than 2 percent of the initial value, for example not more than 1 percent, and for example does not change at all within the experimental error. The method of measurement employed for this is immaterial provided that the same measuring conditions are always used for comparisons.

The viscosity of an aqueous solution is determined using Brookfield viscometers for instance. The solids contents and the spindles to be used vary according to the molar mass of the polymers to be investigated. The measurement and the suitable spindles and weight concentrations of the polymers according to weight-average molecular weight is known as such to a person skilled in the art and has been published and referenced in numerous publications and product brochures, for instance those from BASF regarding polyvinylpyrrolidones for technical applications (brand name "Luvitec®"). However, the only important requirement for assessing the stability of the viscosity is that the same measuring conditions are always used for comparative measurements. The type of measurement is then immaterial for comparing two measured results on two different polymers or differently aged/stored samples of polymer.

Storage preferably takes place in sealed packages in each case. It is more preferable for such sealed packages to be gastight or almost gastight and further also preferably pervious or almost pervious to water passage.

Gas permeability is indicated in relation to a selected reference gas, such as oxygen.

By the ASTM D3985, DIN 53380/3 methods of determination, the packages for storing the polymers have an oxygen permeability of less than 0.5, preferably of less than 0.45 and more preferably of 0.4 $cm^3/(m^2 \times d \times bar)$ or less at 23° C. and 50% relative humidity.

The ASTM D3985 standard, which is used to determine the barrier properties of multilayered structures, describes the constant air permeability rate of EVOH and is determined on foils (test specimens) using coulometers.

The ASTM F1249 water vapor permeability of packaging for storing the polymers is less than 0.5, preferably less than 0.4 and more preferably 0.3 $g/cm^2 \times d$ or lower at a temperature of 23° C. and 85% relative humidity.

According to an alternative method of determination, the water vapor permeation of DIN EN 12086-Climate B is less than 0.5, preferably less than 0.4 and more preferably not more than 0.35 $g/m^2 \times d$.

These gas permeability and water vapor permeability values hold for film bags, film sacks or packages with which the polymer solution, polymer dispersion or the solid polymer come into direct contact. Suitable packaging materials of this type are known from WO 2010/052088 A1. Polymers of one or more embodiments of the present invention which are obtainable by the process of one or more embodiments of the present invention are therefore preferably packed in packages produced from multilayered films using a packaging process wherein the multilayered films, the packages and the packaging processes correspond to those of WO 2010/052088 A1, which is why the disclosure of WO 2010/052088 A1 is hereby fully incorporated herein by reference for the embodiments, preferred, more preferred and even more preferred embodiments disclosed therein for multilayered films, the packages therefrom and the packaging processes for packaging the polymers of one or more embodiments of the present invention for storage and transport, since these are also the preferred, more preferred and even more preferred embodiments in the context of the present invention.

Polymers obtainable by the present process have little to almost no "typical intrinsic odor". When intrinsic odor is minimal, the odor is called "neutral". "Musty" odors, which are known and very common with PVP and vinyllactam polymers, are absent from the present polymers. On the contrary, the low to very low intrinsic/neutral odor undergoes virtually no change on storage, especially even at elevated temperatures of 40° C. or even 50° C. over periods of not less than 3, 6, 9, 12 or more months or even 2 years. More particularly, there is no deterioration in odor. The assessment of odor and the understanding of terms such as "neutral odor", "intrinsic odor", "typical intrinsic odor" and "musty odors" are known to a person skilled in the art.

Preferably, the polymers obtainable by the present process have at least in two, more preferably in three, even more preferably in four and especially in all five properties selected from color, odor, gel content, viscosity and turbidity the properties according to the invention which were indicated above in each case and—preferably—also the combinations of the particular preferred values of these properties.

The polymer obtainable according to one or more embodiments of the present invention, preferably polyvinylpyrrolidone having K values between 20 and 35, preferably in aqueous solution with polymer solids concentrations between 15 and 60 weight percent, preferably produced in aqueous solution, preferably using hydrogen peroxide as initiator, further preferably with ammonium (hydrogen)carbonate, more preferably ammonium hydrogencarbonate, as base before/during the polymerization, and further preferably with ammonia as base for pH raising after the polymerization, is preferably used in cosmetic and pharmaceutical preparations, for instance as storage-stable disinfectant complexed with iodine, as binder, as texture-former and also the other pharmaceutically customary and known fields of use and also as ingredient in hair-cosmetic preparations, such as setting agent in hair gels, especially those having carbomer types as thickeners.

It is further preferable to use the polymer obtainable according to one or more embodiments of the present invention for production of membranes, especially for separation and purification of materials, especially liquids, for instance dialysis membranes and membranes for purification of blood and water. Typical dialysis membranes comprise polysulfones and/or polyether sulfones and PVP, the latter being used inter alia for pore formation and pore size control.

The polymers, especially the polyvinylpyrrolidones, are further useful as laundry detergent additives (e.g., dye transfer inhibitors, soil anti-redeposition agents) and also for numerous technical applications (photoresists, thickeners, adhesives, textile dyeing auxiliaries, glue pens, metal quench baths, separation of noble metals, brighteners, complexes with antioxidants, concrete admixture agents, coating of polyolefins/fibers, printing inks, diazotypes, electroconductive layers, electrode gels, skin-adhesive gels, ultrasound gels, removal of polyvalent cations, removal of polyphenols, enzyme and protein complexes, color-mingling inhibitors, solid batteries, solid electrolytes, fish feed pellets, fixator for perfume oils, flexographic printing plates, flocculants, photographic plates, gas analysis, plaster bandages, lubricants, adhesion promoters for dyes, hydrophilicization of surfaces, ion exchangers, isomerization inhibitor, protective colloid, liquid inks, jet inks, ballpoint pen pastes, catalysts, catheter coating, ceramic binder, scale remover, adhesive for nutrient media, complexation with organic or inorganic compounds to enhance adsorbability/hydrophobicity, complexes with halogen, complexes with polymers, preservatives, contact lenses, corrosion control, plastics additives, paint adjuncts, light-sensitive materials, lithography, solubilization, air filters, metal casting, metal hardening, stabilization of metal colloids, metal complexes for reversible oxygen absorption, microencapsulation, oil and dye removal from water, oil recovery, paper auxiliaries, paper-coating slips, phase transfer catalysts, photoimaging, pigment dispersions, proton conductors, cleaning agents for wastewaters, seed dressing, seed coating, lubricant additives, silver halide emulsions, soil release, stabilization of peroxides, synthetic fibers, tertiary oil production, textile auxiliaries, separation of hydrocarbon mixtures, viscosity modification, heat-resistant layers, heat-sensitive layers, heat-sensitive resistors, water-soluble films, cigarette filters) and in many cases display positive properties over the polymers hitherto available, whether in use, the processing and/or the particular durability of preparations, films and manufactured articles, a simplified formulation or the compatibility in formulations and uses.

The polymers obtainable according to one or more embodiments of the present invention, especially the polymers obtainable via the preferred embodiments 1 to 84, comprise as desired only very low formic acid contents, enzymatically determined as specified in pertinent publications, for instance pharmacopeias, of less than 2000 ppm, preferably less than 1500 ppm, more preferably less than 1200 ppm and even more preferably less than 1100 ppm and especially less than 1000 ppm such as 900 ppm, 800 ppm, 700 ppm or even less, all based on 100 weight percent of polymer.

Polymer obtainable according to the prior art, for instance as described in Examples 1 to 3 of DE 11 2005 00 2719, and also polymers obtained from variants of the present process but which was carried out with prior art acids instead of sulfur component in step e), by contrast, exhibit very much higher values in respect of the parameters relevant to the present invention: formic acid contents, viscosity, color, turbidity, pH, odor show distinctly different, disadvantageous values, as determined and shown in the examples.

Particular advantages of polymers obtainable according to one or more embodiments of the present invention, especially in the case of PVP obtained in one of the preferred embodiments, are more particularly high color stability even in hair gels and especially in clear, colorless gels that typically comprise carbomer-type thickeners. Virtually no discoloration whatsoever was detectable in these gels even on storage at room temperature or higher temperatures.

Gel stability of such hair gels is better than with previous polymers even on storage at elevated temperature. The deviations in respect of viscosity (typically a viscosity decrease) are distinctly less and are negligibly small. Similarly, gel consistency (i.e., the texture of the gel, i.e., whether there are for example structures in the gel or not) is better (that is, texture is less or even completely absent, i.e., the gel is entirely smooth and uncontoured) even after prolonged storage. The stabilities observed for viscosities were up to 10 percent, preferably up to 20 percent, more preferably up to 30 percent, even more preferably up to 40 percent and especially up to 50 percent above those of prior art polymers under the same conditions of measurement.

It was similarly observed that the polymers, especially PVP obtained in one of the preferred embodiments, and hence also their formulations such as hair gels are given a distinctly better odor rating than prior art polymers. The odor of the polymers and of the hair gels is fresher and neutral up to a very slight intrinsic odor. Previously observed comparatively pronounced intrinsic odor or even musty and cornflourlike, moldy odors are not observed with the polymers of one or more embodiments of the present invention.

Furthermore, the pH of the obtainable polymers, especially of PVP obtained in one of the preferred embodiments, is higher than for prior art polymers, which is why the base quantity needed for neutralization comes out less and the polymers and hence the formulations are burdened with less added material such as base.

It was similarly determined that hair setting performance of hair gels, especially those of the carbomer type, comprising polymers of one or more embodiments of the present invention, especially PVP obtained in one of the preferred embodiments 1 to 84 and having in particular a K value between 20 and 35, is up to 10 percent, preferably up to 20 percent, more preferably up to 30 percent, even more preferably up to 40 percent and for example up to 50 percent better than with prior art polymers. A "better" result means that the same setting effect can be achieved with correspondingly less polymer, enabling cost saving and greater freedom in producing the formulation. Alternatively, as will be appreciated, it is also possible to achieve a higher setting effect for the same amount of polymer.

Surprisingly, the polymer powders, especially PVP, which were polymerized using hydrogen peroxide and have more particularly a K value between 20 and 35, were less dusting at comparable flowability despite being dried by spray drying in the same dryer under identical conditions.

Dustability was determined as follows: a glass bottle 250 ml in capacity was ⅔ filled with polymer powder and sealed. The bottle was repeatedly shaken by hand in all directions for half a minute, put down and then the lid taken off: if there were no dust clouds or "smoke" coming out of the open bottle, the polymer powder was rated "nondusting". If there were minimal clouds, the powder was classified as "minimally dusting". For correspondingly more severe dusting, the classifications are "scarcely dusting", "slightly dusting", "dusting" in a correspondingly increasing sequence.

This ability to form dust is particularly relevant for handling such polymer powders in practice, for instance during transfer and formulation.

Polymer obtainable by the process of one or more embodiments of the present invention such as more particularly by one of embodiments 1 to 84 is preferably scarcely dusting, more preferably minimally dusting and most preferably nondusting.

EXAMPLES

Methods of Determination

The methods regarding solids content, pH value, K value, vinylpyrrolidone and sulfate ash are generally described in the "Povidone" monograph in USP and Ph.Eur. Formic acid is generally mentioned in Ph.Eur under residual solvents (class 3). The HAZEN color number is alternatively also referred to as platinum-cobalt color number and described in DIN ISO 6271-1.

The following methods of determination were used for the present examples:

| | |
|---|---|
| Solids content | Dry for 30 minutes in circulating air oven at 140° C., differential weighing provides the solids content |
| pH value (10% in water) | Ph.Eur.7.Edition, 2.2.3, |
| K value (1% (m/v) in water) | to Fikentscher as per Ph.Eur. 7 |
| FTU (10% in water) | to DIN ISO15715 |
| Vinylpyrrolidone | to Ph.Eu.7 |
| Hazen color number | DIN ISO 6271-1 |
| Formic acid | enzymatically |

Example 1

Initially the following solutions were prepared:
1. Initial charge consisting of 1688 g of completely ion-free water, 750 g of N-vinylpyrrolidone and 5.58 g of ammonia water (25% strength)
2. Feed 1, consisting of 8.81 g of hydrogen peroxide (50% strength)
3. Feed 2, consisting of 0.081 g of copper chloride solution (0.091% strength)
4. Feed 3, consisting of 61.5 g of sulfurous acid (6% strength)
5. Feed 4, consisting of 1.9 g of ammonia (25% strength)

The initial charge in a laboratory apparatus made of glass and equipped with a reflux condenser and a half-moon stirrer was heated up to 75° C. under a slow stream of nitrogen and under agitation. When the temperature of 75° C. was reached, feed 1 was added in less than 1 minute followed immediately thereafter by the addition of feed 2. Shortly thereafter an exotherm was observed for the polymer solution, which increased up to 100° C. after 6 minutes under gentle refluxing. The solution was subsequently further stirred at 85° C. for 1 hour. The pH was initially 10 before the $H_2O_2$ was added and 7.2 at the end of the polymerization. The polymer solution was then adjusted with feed 3 to a pH of about 3.6 under agitation. The solution was again heated up to about 100° C. and steam stripped for 1 h to obtain a distillate quantity of 500 g. After steam stripping, the solution was cooled down and neutralized with feed 4.

An almost colorless transparent polymer solution 1 was obtained with the following parameters:

| | |
|---|---|
| Solids content (30 min, 140° C.): | 30.6 wt % |
| pH value (10% in water) | 6 |
| K value (1% (m/v) in water) | 29.6 |
| FTU (10% in water) to DIN ISO15715 | 0.75 |
| Vinylpyrrolidone | <1 ppm |
| Hazen as-obtained | 18 |
| Hazen (3.5% strength solution) | 5 |
| Formic acid (solution) | 220 ppm |
| Formic acid (based on polymer) | 740 ppm |

Example 1a (Comparative Example)

Example 1 was repeated using hydrochloric acid to set the pH below 4 instead of sulfurous acid.

A distinctly yellow polymer solution 1a was obtained with the following parameters:

| | |
|---|---|
| Solids content (30 min, 140° C.) | 30.7 wt % |
| pH value (10% in water) | 6.1 |
| K value (1% (m/v) in water) | 29.8 |
| FTU (10% in water) to DIN ISO15715 | 0.73 |
| Vinylpyrrolidone | <1 ppm |
| Hazen as-obtained | 440 |
| Hazen (3.5% strength solution) | 35 |
| Formic acid (solution) | 210 ppm |
| Formic acid (based on polymer) | 700 ppm |

Example 2

Initially the following solutions were prepared:
1. Initial charge consisting of 1294 g of completely ion-free water, 1125 g of N-vinylpyrrolidone and 8.37 g of ammonia water (25% strength)
2. Feed 1, consisting of 13.2 g of hydrogen peroxide (50% strength)
3. Feed 2, consisting of 0.121 g of copper chloride solution (0.091% strength)
4. Feed 3, consisting of 68.1 g of sulfurous acid (6% strength)
5. Feed 4, consisting of 5.4 g of ammonia (25% strength)

The initial charge in a laboratory apparatus made of glass and equipped with a reflux condenser and a half-moon stirrer was heated up to 75° C. under a slow stream of nitrogen and under agitation. When the temperature of 75° C. was reached, feed 1 was added in less than 1 minute followed immediately thereafter by the addition of feed 2. Shortly thereafter a violent exotherm was observed for the polymer solution, which increased up to 100° C. after 3 minutes under severe refluxing. The solution was subsequently further stirred at 85° C. for 1 hour. The pH was initially 10.6 before the $H_2O_2$ was added and 6.2 at the end of the polymerization. The polymer solution was then adjusted with feed 3 to a pH of about 3.8 under agitation. The solution was again heated up to about 100° C. and steam stripped for 45 min to obtain a distillate quantity of 200 g. After steam stripping, the solution was cooled down and neutralized with feed 4.

An almost colorless transparent polymer solution 2 was obtained with the following parameters:

| | |
|---|---|
| Solids content (30 min, 140° C.) | 44.2 wt % |
| pH value (10% in water) | 7.4 |
| K value (1% (m/v) in water) | 29.4 |
| FTU (10% in water) to DIN ISO15715 | 0.54 |
| Vinylpyrrolidone | <1 ppm |
| Hazen as-obtained | 30 |
| Hazen (3.5% strength solution) | 5 |
| Formic acid (solution) | 365 ppm |
| Formic acid (based on polymer) | 830 ppm |

Example 2a (Comparative Example)

Example 2 was repeated using sulfuric acid to set the pH below 4 instead of sulfurous acid.

A distinctly yellow polymer solution 2a was obtained with the following parameters:

| | |
|---|---|
| Solids content (30 min, 140° C.) | 44.0 wt % |
| pH value (10% in water) | 7.8 |
| K value (1% (m/v) in water) | 29.7 |
| FTU (10% in water) to DIN ISO15715 | 0.73 |
| Vinylpyrrolidone | <1 ppm |
| Hazen as-obtained | 580 |
| Hazen (3.5% strength solution) | 37 |
| Formic acid (solution) | 460 ppm |
| Formic acid (based on polymer) | 1050 ppm |

Example 3

Initially the following solutions were prepared:
1. Initial charge consisting of 1294 g of completely ion-free water, 1125 g of N-vinylpyrrolidone and 8.37 g of ammonia water (25% strength)
2. Feed 1, consisting of 17.8 g of hydrogen peroxide (50% strength)
3. Feed 2, consisting of 0.121 g of copper chloride solution (0.091% strength)
4. Feed 3, consisting of 60.4 g of sulfurous acid (6% strength)
5. Feed 4, consisting of 4.8 g of ammonia (25% strength)

The initial charge in a laboratory apparatus made of glass and equipped with a reflux condenser and a half-moon stirrer was heated up to 73° C. under a slow stream of nitrogen and under agitation. When the temperature of 73° C. was reached, feed 1 was added in less than 1 minute followed immediately thereafter by the addition of feed 2. Shortly thereafter a violent exotherm was observed for the polymer solution, which increased up to 100° C. after 4 minutes under severe refluxing. The solution was subsequently further stirred at 85° C. for 1 hour. The pH was initially 10.8 before the $H_2O_2$ was added and 5.0 at the end of the polymerization. The polymer solution was then adjusted with feed 3 to a pH of about 3.8 under agitation. The solution was again heated up to about 100° C. and steam stripped for 1 h to obtain a distillate quantity of 200 g. After steam stripping, the solution was cooled down and neutralized with feed 4.

An almost colorless transparent polymer solution 3 was obtained with the following parameters:

| | |
|---|---|
| Solids content (30 min, 140° C.) | 43.6 wt % |
| pH value (10% in water) | 6.8 |
| K value (1% (m/v) in water) | 24.5 |
| FTU (10% in water) to DIN ISO15715 | 0.52 |
| Vinylpyrrolidone | <1 ppm |
| Hazen as-obtained | 75 |
| Hazen (3.5% strength solution) | 6 |
| Formic acid (solution) | 445 ppm |
| Formic acid (based on polymer) | 1020 ppm |

Example 3a (Comparative Example)

Example 5 was repeated using sulfuric acid to set the pH below 4 instead of sulfurous acid.

A distinctly yellow polymer solution 3a was obtained with the following parameters:

| | |
|---|---|
| Solids content (30 min, 140° C.) | 43.7 wt % |
| pH value (10% in water) | 6.8 |
| K value (1% (m/v) in water) | 24.4 |
| FTU (10% in water) to DIN ISO 15715 | 0.55 |
| Vinylpyrrolidone | <1 ppm |
| Hazen as-obtained | 620 |
| Hazen (3.5% strength solution) | 41 |
| Formic acid (solution) | 450 ppm |
| Formic acid (based on polymer) | 1030 ppm |

Example 4

Initially the following solutions were prepared:
1. Initial charge consisting of 1640 g of completely ion-free water, 800 g of N-vinylpyrrolidone and 2.7 g of ammonium hydrogencarbonate
2. Feed 1, consisting of 9.4 g of hydrogen peroxide (50% strength)
3. Feed 2, consisting of 0.086 g of copper chloride solution (0.091% strength)
4. Feed 3, consisting of 34.3 g of sulfurous acid (6% strength)
5. Feed 4, consisting of 1.9 g of ammonia (25% strength)

The initial charge in a laboratory apparatus made of glass and equipped with a reflux condenser and a half-moon stirrer was heated up to 74° C. under a slow stream of nitrogen and under agitation. When the temperature of 74° C. was reached, feed 1 was added in less than 1 minute followed immediately thereafter by the addition of feed 2. Shortly thereafter an exotherm was observed for the polymer solution, which increased up to 100° C. after 10 minutes under gentle refluxing. The solution was subsequently further stirred at 85° C. for 1 hour. The pH was initially 8.0 before the $H_2O_2$ was added and 6.2 at the end of the polymerization. The polymer solution was then adjusted with feed 3 to a pH of about 3.7 under agitation. The solution was again heated up to about 100° C. and steam stripped for 1 h to obtain a distillate quantity of 450 g. After steam stripping, the solution was cooled down and neutralized with feed 4.

An almost colorless transparent polymer solution 4 was obtained with the following parameters:

| | |
|---|---|
| Solids content (30 min, 140° C.) | 31.7 wt % |
| pH value (10% in water) | 7.7 |
| K value (1% (m/v) in water) | 28.4 |
| FTU (10% in water) to DIN ISO15715 | 0.49 |
| Vinylpyrrolidone | <1 ppm |
| Hazen as-obtained | 20 |
| Hazen (3.5% strength solution) | 5 |
| Formic acid (solution) | 230 ppm |
| Formic acid (based on polymer) | 730 ppm |

Example 5

Initially the following solutions were prepared:
1. Initial charge consisting of 1688 g of completely ion-free water, 750 g of N-vinylpyrrolidone and 2.5 g of sodium carbonate
2. Feed 1, consisting of 8.8 g of hydrogen peroxide (50% strength)
3. Feed 2, consisting of 0.081 g of copper chloride solution (0.091% strength)
4. Feed 3, consisting of 39.9 g of sulfurous acid (6% strength)
5. Feed 4, consisting of 2.2 g of ammonia (25% strength)

The initial charge in a laboratory apparatus made of glass and equipped with a reflux condenser and a half-moon stirrer was heated up to 73° C. under a slow stream of nitrogen and under agitation. When the temperature of 73° C. was reached, feed 1 was added in less than 1 minute followed immediately thereafter by the addition of feed 2. Shortly thereafter an exotherm was observed for the polymer solution, which increased up to 100° C. after 10 minutes under gentle refluxing. The solution was subsequently further stirred at 85° C. for 1 hour. The pH was initially 11.2 before the $H_2O_2$ was added and 6.8 at the end of the polymerization. The polymer solution was then adjusted with feed 3 to a pH of about 3.9 under agitation. The solution was again heated up to about 100° C. and steam stripped for 1 h to obtain a distillate quantity of 260 g. After steam stripping, the solution was cooled down and neutralized with feed 4.

An almost colorless transparent polymer solution 5 was obtained with the following parameters:

| | |
|---|---|
| Solids content (30 min, 140° C.) | 30.0 wt % |
| pH value (10% in water) | 5.9 |
| K value (1% (m/v) in water) | 32.2 |
| FTU (10% in water) to DIN ISO15715 | 0.48 |
| Vinylpyrrolidone | 4 ppm |
| Hazen as-obtained | 18 |
| Hazen (3.5% strength solution) | 5 |
| Formic acid (solution) | 210 ppm |
| Formic acid (based on polymer) | 700 ppm |

Example 6

Initially the following solutions were prepared:
1. Initial charge consisting of 1737 g of completely ion-free water, 1000 g of N-vinylpyrrolidone and 3.72 g of ammonia water (25% strength)
2. Feed 1, consisting of 10.6 g of hydrogen peroxide (50% strength)
3. Feed 2, consisting of 0.107 g of copper chloride solution (0.091% strength)
4. Feed 3, consisting of 55.6 g of sulfurous acid (6% strength)
5. Feed 4, consisting of 3.5 g of ammonia (25% strength)

The initial charge in a laboratory apparatus made of glass and equipped with a reflux condenser and a half-moon stirrer was heated up to 50° C. under a slow stream of nitrogen and under agitation. When the temperature of 50° C. was reached, feed 1 was added in less than 1 minute followed immediately thereafter by the addition of feed 2. Shortly thereafter an exotherm was observed for the polymer solution, which increased up to 100° C. after 15 minutes under moderate refluxing. The solution was subsequently further stirred at 80° C. for 1 hour. The polymer solution was then adjusted with feed 3 to a pH of about 3.6 under agitation. The solution was again heated up to about 100° C. and steam stripped for 1 h to obtain a distillate quantity of 400 g. After steam stripping, the solution was cooled down and neutralized with feed 4 and adjusted with water to a solids content of 30%.

An almost colorless polymer solution 6 was obtained with the following parameters:

| | |
|---|---|
| Solids content (30 min, 140° C.) | 29.8 wt % |
| pH value (10% in water) | 8.4 |
| K value (1% (m/v) in water) | 32.3 |
| FTU (10% in water) to DIN ISO15715 | 0.44 |
| Vinylpyrrolidone | <1 ppm |
| Hazen as-obtained | 19 |
| Hazen (3.5% strength solution) | 6 |
| Formic acid (solution) | 225 ppm |
| Formic acid (based on polymer) | 750 ppm |

The solution was dried by means of spray drying to give a powder. After redissolving the powder to give an aqueous solution, gel permeation chromatography (GPC) was used to determine the molecular parameters of the polymer, such as number-average molecular weight $M_n$, mass-average molecular weight $M_w$, and the resulting polydispersity index D.

The GPC analysis used an

SEC apparatus: App_L

Eluent: water/acetonitrile (80/20)+0.15 mol/l NaCl+0.03 mol/l NaH2PO4 adjusted to pH=9

Column temperature: 35° C.

Flow rate: 0.8 mL/min

Injection: 100 μL

Concentration: 1.5 mg/mL

Sample solutions were filtered through Millipore IC Millex-LG (0.2 μm).

Separation Column Combination

| | Columns | | | | |
|---|---|---|---|---|---|
| No. | i.d. mm | Length cm | Separation material | Exclusion limit g/mol | Column name |
| 1171 | 8 | 30 | Suprema-Gel(HEMA) | | Suprema linear S |
| 1170 | 8 | 30 | Suprema-Gel(HEMA) | | Suprema linear XL |

Number of plates for the combination at the flow rate reported: 40 000

Detector: UV Agilent 1200 VWD [208 nm]

Calibration: The calibration was effected with the narrow-distribution polyvinylpyrrolidone standards from Polymer American Standards, USA with molecular weights of M=4300 to M=1 065 000.

The values outside this elution range were extrapolated.

The following values were obtained for the polymer prepared according to example 6:

$M_n$ (g/mol) 14 600
$M_w$ (g/mol) 46 000
D: 3.2

As a comparison, the molecular parameters of commercially available PVP K30 were determined under identical conditions:

$M_n$ (g/mol) 12 500
$M_w$ (g/mol) 55 800
D: 4.5

Example 7

Initially the following solutions were prepared:
1. Initial charge consisting of 1955 g of completely ion-free water, 1150 g of N-vinylpyrrolidone and 4.6 g of 2-amino-2-methyl-1-propanol (AMP 95)
2. Feed 1, consisting of 11.7 g of hydrogen peroxide (50% strength)
3. Feed 2, consisting of 0.123 g of copper chloride solution (0.091% strength)
4. Feed 3, consisting of 66.7 g of sulfurous acid (6% strength)
5. Feed 4, consisting of 4.4 of 2-amino-2-methyl-1-propanol (AMP 95)

The initial charge in a laboratory apparatus made of glass and equipped with a reflux condenser and a half-moon stirrer was heated up to 75° C. under a slow stream of nitrogen and under agitation. When the temperature of 75° C. was reached, feed 1 was added in less than 1 minute followed immediately thereafter by the addition of feed 2. This was followed by further heating to 80° C. and shortly thereafter an exotherm was observed for the polymer solution. The solution was subsequently further stirred at 80° C. for 1 hour. The polymer solution was then adjusted with feed 3 to a pH of about 3.6 under agitation. The solution was again heated up to about 100° C. and steam stripped for 1 hour. After steam stripping, the solution was cooled down and neutralized with feed 4.

An almost colorless polymer solution 7 was obtained with the following parameters:

| | |
|---|---|
| Solids content (30 min, 140° C.) | 37.5 wt % |
| pH (10% in water) | 6.4 |
| K value (1% (m/v) in water) | 32.1 |
| FTU (10% in water) to DIN ISO15715 | 0.45 |
| Vinylpyrrolidone | <1 ppm |
| Hazen as-obtained | 13 |
| Hazen (3.5% strength solution) | 3 |

The polymers of Examples 1, 2 and 3 of DE 11 2005 002 719 were produced and analyzed:

| | Examples 1/2/3 |
|---|---|
| Solids content | 49.1/49.1/49.2 |
| K value | 23/23.5/25.8 |
| HAZEN (as-obtained) | 180/210/160 |
| HAZEN (3.5% strength solution) | 12/15/10 |
| Formic acid solution | 4000/3700/3600 ppm |
| Formic acid (based on polymer) | 8150/7550/7300 ppm |

Polymers solutions 1-6 of the present invention were stored at 40° C. for three months together with the polymer solutions produced as described in Examples 1 to 3 of DE 11 2005 002 719 and the HAZEN color value was measured on a 3.5% strength solution after 1, 2 and 3 months (Table 1).

TABLE 1

Examples 1 to 6, comparative examples from DE 11 2005 002 719

| HAZEN color number/polymer solution | Initial value | HAZEN color number after 1 month | HAZEN color number after 2 months | HAZEN color number after 3 months | Observation |
|---|---|---|---|---|---|
| 1 | 5 | 5 | 6 | 6 | 1 |
| 2 | 5 | 6 | 6 | 7 | 1 |
| 3 | 6 | 5 | 6 | 6 | 1 |
| 4 | 5 | 6 | 6 | 7 | 1 |
| 5 | 5 | 5 | 5 | 6 | 1 |
| 6 | 5 | 5 | 6 | 6 | 1 |
| Example 1 (DE) | 12 | 15 | 20 | 26 | 2 |
| Example 2 (DE) | 15 | 17 | 18 | 30 | 2 |
| Example 3 (DE) | 10 | 15 | 20 | 24 | 2 |

Observations 1: no color change

Observations 2: severe discoloration

Aqueous polymer solutions obtained according to Inventive Examples 3 and 4 and a solution obtained according to Comparative Example 3a

| | Odor, clarity and color - at as-obtained polymer solids content | | |
|---|---|---|---|
| | | after 4 weeks' storage at | |
| Polymer | as prepared | 25° C. | 40° C. |
| Solution from Example 3a | clear, yellow not OK (color) odor: not very intensive, minimally terpenelike, minimally sweetish, not moldy; OK overall verdict: not OK (color) | yellow, clear not OK (color) odor: not very intensive, minimally terpenelike, OK overall verdict: not OK (color) | intensively yellow, clear not OK (color) odor: not very intensive, minimally terpenelike, minimally cornflourlike; still OK overall verdict: not OK (color) |
| Solution from Example 3 | colorless, almost clear OK odor: not very intensive, fresh, minimally terpenelike, minimally dry yeast, better than standard; OK overall verdict: OK | almost clear, colorless OK odor: not very intensive, minimally dry yeastlike, minimally terpenelike, pleasant; OK overall verdict: OK | clear, almost colorless; OK odor: not very intensive, minimally terpenelike, minimally dry yeastlike OK overall verdict: OK. |
| Solution from Example 4 | colorless, clear; OK odor: not very intensive, minimally terpenelike, minimally dry yeast, pleasant, better than standard; OK overall verdict: OK | clear/almost clear, colorless OK odor: not very intensive, minimally dry yeastlike, minimally terpenelike; OK overall verdict: OK | almost colorless, almost clear OK-still OK (color) odor: not very intensive, minimally dry yeastlike, minimally terpenelike; OK overall verdict: OK-still OK (color) |

Aqueous polymer solutions obtained according to Inventive Examples 3 and 4 and a solution obtained according to Comparative Example 3a

| | Odor, clarity and color - at 5 wt % polymer solids content | | |
|---|---|---|---|
| | | after 4 weeks' storage at | |
| Polymer | as prepared | 25° C. | 40° C. |
| Solution from Example 3a | clear, very minimally yellowish still OK odor: not very intensive, not moldy, slightly flowery, fresh, pleasant OK overall verdict: still OK | minimally yellowish, clear borderline not OK (color) odor: not very intensive, fresh, slightly terpenelike OK overall verdict: not OK (color) | slightly yellowish-yellowish, clear; not OK (color) odor: not very intensive, minimally terpenelike, minimally flowery, not moldy, no cornflour OK overall verdict: not OK (color) |
| Solution from Example 3 | clear, colorless OK odor: not very intensive, minimally dry yeast, pleasant, less intensive/better than standard OK overall verdict: OK. | clear, colorless OK odor: not very intensive, minimally flowery, terpenelike, fresh; OK overall verdict: OK. | clear, colorless OK odor: not very intensive, minimally terpenelike, not moldy, no cornflour, fresh; OK overall verdict: OK. |
| Solution from Example 4 | clear, colorless; OK odor: almost odorless, minimal dry yeast odor, pleasant, less intensive/better than standard; OK overall verdict: OK. | clear, colorless; OK odor: not very intensive, minimally terpenelike, fresh, similar to standard OK overall verdict: OK | clear, colorless; OK odor: not very intensive, minimally terpenelike, not moldy, no cornflour, OK overall verdict: OK |

Aqueous polymer solutions obtained according to Inventive Examples 3 and 4 and a solution obtained according to Comparative Example 3a

| pH - at as-obtained polymer solids content | | | |
|---|---|---|---|
| | | after 4 weeks' storage at | |
| Polymer | as prepared | 25° C. | 40° C. |
| Solution from Example 3a | 4.7 | 4.7 | 4.6 |
| Solution from Example 3 | 7.25 | 7.7 | 7.3 |
| Solution from Example 4 | 7.5 | 7.9 | 7.75 |

| Hair gels from polymer solutions | | | |
|---|---|---|---|
| | | after 4 weeks' storage at | |
| PVP K 30 | as prepared | 25° C. | 40° C. |
| Solution from Example 3a | minimally yellowish, slightly bluish, firm gel not OK (color) odor: typically Carbopol; OK overall verdict: not OK (color) | slightly yellowish, minimally bluish, still firm gel; not OK (color) odor: not very intensive, typically Carbopol; OK overall verdict: not OK (color) | yellow, minimally bluish, still firm gel; not OK (color) odor: intensive Carbopol odor; still OK overall verdict: not OK (color) |
| Solution from Example 3 | colorless, slightly bluish, firm gel; OK odor: not very intensive, typically Carbopol; OK overall verdict: OK | absolutely colorless, slightly bluish, firm gel OK odor: not very intensive, typically Carbopol; OK overall verdict: OK | colorless, minimally bluish, firm gel; OK not very intensive, typically Carbopol; OK overall verdict: OK |
| Solution from Example 4 | colorless, slightly bluish, firm gel; OK odor: not very intensive, typically Carbopol; OK overall verdict: OK | colorless, minimally bluish, firm gel; OK odor: not very intensive, typically Carbopol; OK overall verdict: OK | colorless, slightly bluish, firm gel; OK odor: not very intensive, typically Carbopol; OK overall verdict: OK |

5% polymer content in Carbopol 980 (0.5%). All tests use the same base-gel recipe. Base gel adjusted to pH 7 with triethylamine and preserved with Euxyl K 100.

Hair Gels from Polymer Solutions. Stability in Storage

5% polymer content in Carbopol 980 (0.5%). All tests use the same base-gel recipe. Base gel adjusted to pH 7 with triethylamine and preserved with Euxyl K 100.

| | as prepared | | | |
|---|---|---|---|---|
| Polymer | Bending test mean [cN]** | Curl retention [%] | Viscosity [mPas] | pH |
| Solution from Example 3a | 62 (58-67) | 37 | 26700 | 6.5 |
| Solution from Example 3 | 87 (81-92) | 39 | 23800 | 6.65 |
| Solution from Example 4 | 83 (79-87) | 34 | 25050 | 6.65 |

**Bending test data between parentheses: measured-value span of 5 or more strands

| | after 4 weeks | | | |
|---|---|---|---|---|
| | viscosity [mPas] | | pH | |
| Polymer | RT | 40° C. | RT | 40° C. |
| Solution from Example 3a | 23100 | 21650 | 6.5 | 6.5 |
| Solution from Example 3 | 22500 | 23000 | 6.6 | 6.6 |
| Solution from Example 4 | 24500 | 24850 | 6.7 | 6.6 |

Aqueous polymer solutions obtained according to Inventive Examples 3 and 4 and a solution obtained according to Comparative Example 3a, after drying to the powder via spray drying in air

| | | after 4 weeks' storage at | |
|---|---|---|---|
| Polymer | as prepared | 25° C. | 40° C. |
| | Odor, color, dustability, flowability | | |
| Polymer from Example 3a | very minimally yellowish, crystalline, free-flowing powder, dusts; still OK odor: almost odorless; OK overall verdict: still OK | almost white - minimally cream-colored, free flowing, minimally dusting; OK odor: almost odorless, minimally moldy; OK overall verdict: OK | cream-colored - very minimally yellowish, free flowing, slightly dusting - dusting; still OK (color) odor: almost odorless; OK overall verdict: still OK (color) |
| Polymer from Example 3 | white, crystalline, free-flowing powder, slightly dusting OK; odor: almost odorless; OK overall verdict: OK | almost white, free flowing, cf. standard, scarcely dusting; OK odor: not very intensive, minimally moldy/cornflourlike, still OK overall verdict: OK | almost white - minimally cream-colored, better than standard, free flowing, scarcely dusting OK odor: almost odorless; OK overall verdict: OK |
| Polymer from Example 4 | white, crystalline, free-flowing powder, slightly dusting OK odor: almost odorless; OK overall verdict: OK | almost white, free flowing, cf. standard, minimally dusting; OK odor: not very intensive, scarcely moldy; OK overall verdict: OK | almost white - minimally cream-colored, free flowing, minimally dusting; OK odor: almost odorless; OK overall verdict: OK |

Aqueous polymer solutions obtained according to Inventive Examples 3 and 4 and a solution obtained according to Comparative Example 3a, after drying to the powder via spray drying in air and redissolving the powder into an aqueous solution

| | | after 4 weeks' storage at | |
|---|---|---|---|
| Polymer | as prepared | 25° C. | 40° C. |
| | Odor, clarity and color - at 5 wt % polymer solids content | | |
| Polymer from Example 3a | very minimally yellowish (better than standard solution), clear; still OK odor: almost odorless, minimally terpenelike, fresh, pleasant; OK overall verdict: still OK | minimally yellowish, clear borderline not OK (color) odor: not very intensive, minimally terpenelike, minimally flowery; OK overall verdict: borderline not OK (color) | minimally yellowish, cf. Rt, clear; borderline not OK (color) odor: not very intensive, minimally terpenelike, minimally flowery; OK overall verdict: borderline not OK (color) |
| Polymer from Example 3 | colorless, clear; OK odor: not very intensive, not moldy, minimally fruity, pleasant; OK overall verdict: OK | colorless, clear; OK odor: not very intensive, minimally terpenelike, minimally flowery, slightly sweetish; OK overall verdict: OK | colorless, clear; OK odor: not very intensive, minimally terpenelike, minimally flowery; OK overall verdict: OK |
| Polymer from Example 4 | colorless, clear; OK odor: almost odorless, minimally terpenelike, fresh, pleasant; OK overall verdict: OK | colorless, clear; OK odor: almost odorless; OK overall verdict: OK | colorless, clear; OK odor: almost odorless; OK overall verdict: OK |

| | pH at 5 wt % polymer solids content | | |
|---|---|---|---|
| | | after 4 weeks' storage at | |
| Polymer | as prepared | 25° C. | 40° C. |
| Polymer from Example 3a | 3.8 | 3.7 | 3.6 |
| Polymer from Example 3 | 3.8 | 3.5 | 3.45 |
| Polymer from Example 4 | 3.45 | 3.2 | 3.2 |

Hair Gels from Powders—Stability in Storage

Aqueous polymer solutions obtained according to Inventive Examples 3 and 4 and a solution obtained according to Comparative Example 3a, after drying to the powder via spray drying in air and redissolving the powder into an aqueous solution 5% polymer content in Carbopol 980 (0.5%). All tests use the same base-gel recipe. Base gel adjusted to pH 7 with triethylamine and preserved with Euxyl K 100.

| | | after 4 weeks' storage at | |
|---|---|---|---|
| Polymer | as prepared | 25° C. | 40° C. |
| Polymer from Example 3a | very minimally yellowish (less yellowish than K30L standard), bluish, still firm gel; still OK<br>not very intensive, typically Carbopol; OK<br>overall verdict: still OK | minimally yellowish, slightly bluish, slightly deliquescent gel; not OK (visco and color)<br>not very intensive, typically Carbopol; OK<br>overall verdict: not OK (viscosity, color) | yellowish, slightly bluish, slightly deliquescent gel; not OK (visco and color)<br>intensive Carbopol odor still OK<br>overall verdict: not OK (visco, color) |
| Polymer from Example 3 | colorless, almost clear - minimally bluish, firm gel; OK<br>not very intensive, typically Carbopol; OK<br>overall verdict: OK (better than standard in visco and turbidity) | almost colorless/very minimally yellowish, almost clear, firm gel; OK<br>not very intensive, typically Carbopol; OK<br>overall verdict: OK | almost colorless, very minimally bluish, firm gel<br>OK;<br>not very intensive, typically Carbopol; OK<br>overall verdict: OK |
| Polymer from Example 4 | very minimally yellowish, almost clear/minimally bluish, still firm gel; still OK<br>not very intensive, typically Carbopol; OK<br>overall verdict: still OK (color) | almost colorless/very minimally yellowish, almost clear/very minimally bluish, firm gel;<br>OK/still OK (color)<br>not very intensive, typically Carbopol; OK<br>overall verdict: OK/still OK (color) | almost colorless/very minimally yellowish, almost clear/very minimally bluish, firm gel;<br>OK/still OK (color)<br>not very intensive, typically Carbopol; OK<br>overall verdict: OK/still OK (color) |

| | as prepared | | | |
|---|---|---|---|---|
| Polymer | Bending test mean [cN]** | Curl retention [%] | Viscosity [mPas] | pH |
| Polymer from Example 3a | 67 (63-71) | 33 | 19100 | 6.5 |
| Polymer from Example 3 | 90 (86-95) | 34 | 25350 | 6.55 |
| Polymer from Example 4 | 91 (88-95) | 33 | 24250 | 6.5 |

**Bending test data between parentheses: measured-value span of 5 or more strands

| | after 4 weeks | | | |
|---|---|---|---|---|
| | viscosity [mPas] | | pH | |
| Polymer | RT | 40° C. | RT | 40° C. |
| Polymer from Example 3a | 14850 | 13800 | 6.35 | 6.4 |
| Polymer from Example 3 | 24300 | 25100 | 6.5 | 6.5 |
| Polymer from Example 4 | 23050 | 23450 | 6.3 | 6.4 |

Comparison versus DE 10 2005 00 5974 (Example 3 from DE 10 2005 00 5974, which discloses this example as comparison versus GB 836,831).

A 20% aqueous solution of polyvinylpyrrolidone having a K value of 30 (measured in a 1 wt % aqueous solution) was admixed at 80° C. with 0.1 wt % of sulfur dioxide based on polymer (as a 6% solution of sulfur dioxide in water) 10 and the solution was stirred for one hour. The solution was then cooled down to 40° C. and spray dried. The pulverulent polyvinylpyrrolidone was subsequently sealed into sacks made of aluminum composite foil by flooding the filled sack with nitrogen twice before sealing, and the sealed sack was stored under 15 different conditions. Samples were also sealed in under air and then stored at 25° C. Peroxide content was determined directly after treatment and after three and six months' storage.

TABLE

| Example 3 from DE 10 2005 00 5974; peroxide content in ppm (based on polymer solids content) | | | |
|---|---|---|---|
| | Packed under | | |
| | air | nitrogen | nitrogen |
| Storage at | 25° C. | at 25° C./ 60% RH | at 40° C./75% RH |
| Blank value | <1 | <1 | <1 |
| 3 months | 339 | 383 | 390 |
| 6 months | 458 | 459 | 354 |

Peroxide content is a measure of polymer oxidation. It is known in the art that PVP yellows on oxidation. The high peroxide contents for tests from DE 10 2005 00 5974 correlate with high color values. This shows that the addition of sulfur dioxide alone does not lead to good color values and especially not to good stability in storage.

Comparison Versus GB 836,831

The pH values of aqueous solutions of K 30 PVP were determined as described in GB 836,831. The solution had a solids content of 10 weight percent based on solid polymer. The pH of the solution was then adjusted to 8.01 with triethanolamine and this solution was admixed with 0.5 weight percent of sulfur dioxide or sodium hydrogensulfite (based on solid polymer).

The pH was 7.76 on using sulfur dioxide and 7.68 on using sodium hydrogensulfite.

This shows that the tests as per GB 836,831 provide virtually no lowering in pH on adding the sulfur component. Therefore, solely adding the sulfur component will also not provide any lowering to a pH where an acidic hydrolysis would take place.

Overview of Inventive Embodiments

| Embodiment No. | Based on embodiment No. | Implemented steps | | | | | | | | Base in step b) | Sulfur component in step e) | Process consisting only of steps a) to h)? |
|---|---|---|---|---|---|---|---|---|---|---|---|---|
| | | a | b | c | d | e | d (1) | f | g | h | | | |
| A 1 | | x | o | o | o | x | o | o | o | o | bw | sw | |
| A 2 | | x | x | o | o | x | o | o | o | o | bw | sw | |
| 1 | | x | x | o | x | x | o | o | o | o | bw | sw | |
| 2 | | x | x | o | x | x | o | x | o | o | bw | sw | |
| 3 | | x | x | o | x | x | o | o | x | o | bw | sw | |
| 4 | | x | x | o | x | x | o | o | o | x | bw | sw | |
| 5 | | x | x | n | x | x | o | o | o | o | bw | sw | |
| 6 | | x | x | n | x | x | o | x | x | x | bw | sw | |
| 7 | | x | x | n | x | x | x | x | x | x | bw | sw | |
| 8 | 1 | x | x | o | x | x | o | o | o | o | AHC | sw | |
| 9 | 2 | x | x | o | x | x | o | x | o | o | AHC | sw | |
| 10 | 3 | x | x | o | x | x | o | o | x | o | AHC | sw | |
| 11 | 4 | x | x | o | x | x | o | o | o | x | AHC | sw | |
| 12 | 5 | x | x | n | x | x | o | o | o | o | AHC | sw | |
| 13 | 6 | x | x | n | x | x | o | x | x | x | AHC | sw | |
| 14 | 7 | x | x | n | x | x | x | x | x | x | AHC | sw | |
| 15 | 1 | x | x | o | x | x | o | o | o | o | NH3 | sw | |
| 16 | 2 | x | x | o | x | x | o | x | o | o | NH3 | sw | |
| 17 | 3 | x | x | o | x | x | o | o | x | o | NH3 | sw | |
| 18 | 4 | x | x | o | x | x | o | o | o | x | NH3 | sw | |
| 19 | 5 | x | x | n | x | x | o | o | o | o | NH3 | sw | |
| 20 | 6 | x | x | n | x | x | o | x | x | x | NH3 | sw | |
| 21 | 7 | x | x | n | x | x | x | x | x | x | NH3 | sw | |
| 22 | 1 | x | x | o | x | x | o | o | o | o | bw | SO2 | |
| 23 | 2 | x | x | o | x | x | o | x | o | o | bw | SO2 | |
| 24 | 3 | x | x | o | x | x | o | o | x | o | bw | SO2 | |
| 25 | 4 | x | x | o | x | x | o | o | o | x | bw | SO2 | |
| 26 | 5 | x | x | n | x | x | o | o | o | o | bw | SO2 | |
| 27 | 6 | x | x | n | x | x | o | x | x | x | bw | SO2 | |
| 28 | 7 | x | x | n | x | x | x | x | x | x | bw | SO2 | |
| 29 | 8 | x | x | o | x | x | o | o | o | o | AHC | SO2 | |
| 30 | 9 | x | x | o | x | x | o | x | o | o | AHC | SO2 | |
| 31 | 10 | x | x | o | x | x | o | o | x | o | AHC | SO2 | |
| 32 | 11 | x | x | o | x | x | o | o | o | x | AHC | SO2 | |
| 33 | 12 | x | x | n | x | x | o | o | o | o | AHC | SO2 | |
| 34 | 13 | x | x | n | x | x | o | x | x | x | AHC | SO2 | |
| 35 | 14 | x | x | n | x | x | x | x | x | x | AHC | SO2 | |
| 36 | 15 | x | x | o | x | x | o | o | o | o | NH3 | SO2 | |
| 37 | 16 | x | x | o | x | x | o | x | o | o | NH3 | SO2 | |
| 38 | 17 | x | x | o | x | x | o | o | x | o | NH3 | SO2 | |
| 39 | 18 | x | x | o | x | x | o | o | o | x | NH3 | SO2 | |
| 40 | 19 | x | x | n | x | x | o | o | o | o | NH3 | SO2 | |
| 41 | 20 | x | x | n | x | x | o | x | x | x | NH3 | SO2 | |
| 42 | 21 | x | x | n | x | x | x | x | x | x | NH3 | SO2 | |
| 43 | 1 | x | x | o | x | x | o | o | o | o | bw | sw | yes |
| 44 | 2 | x | x | o | x | x | o | x | o | o | bw | sw | yes |
| 45 | 3 | x | x | o | x | x | o | o | x | o | bw | sw | yes |
| 46 | 4 | x | x | o | x | x | o | o | o | x | bw | sw | yes |
| 47 | 5 | x | x | n | x | x | o | o | o | o | bw | sw | yes |
| 48 | 6 | x | x | n | x | x | o | x | x | x | bw | sw | yes |
| 49 | 7 | x | x | n | x | x | x | x | x | x | bw | sw | yes |
| 50 | 8 | x | x | o | x | x | o | o | o | o | AHC | sw | yes |
| 51 | 9 | x | x | o | x | x | o | x | o | o | AHC | sw | yes |
| 52 | 10 | x | x | o | x | x | o | o | x | o | AHC | sw | yes |
| 53 | 11 | x | x | o | x | x | o | o | o | x | AHC | sw | yes |
| 54 | 12 | x | x | n | x | x | o | o | o | o | AHC | sw | yes |
| 55 | 13 | x | x | n | x | x | o | x | x | x | AHC | sw | yes |

| Embodiment No. | Based on embodiment No. | a | b | c | d | e | d (1) | f | g | h | Base in step b) | Sulfur component in step e) | Process consisting only of steps a) to h)? |
|---|---|---|---|---|---|---|---|---|---|---|---|---|---|
| 56 | 14 | x | x | n | x | x | x | x | x | x | AHC | sw | yes |
| 57 | 15 | x | x | o | x | x | o | o | o | o | NH3 | sw | yes |
| 58 | 16 | x | x | o | x | x | o | x | o | o | NH3 | sw | yes |
| 59 | 17 | x | x | o | x | x | o | o | x | o | NH3 | sw | yes |
| 60 | 18 | x | x | o | x | x | o | o | o | x | NH3 | sw | yes |
| 61 | 19 | x | x | n | x | x | o | o | o | o | NH3 | sw | yes |
| 62 | 20 | x | x | n | x | x | o | x | x | x | NH3 | sw | yes |
| 63 | 21 | x | x | n | x | x | x | x | x | x | NH3 | sw | yes |
| 64 | 22 | x | x | o | x | x | o | o | o | o | bw | SO2 | yes |
| 65 | 23 | x | x | o | x | x | o | x | o | o | bw | SO2 | yes |
| 66 | 24 | x | x | o | x | x | o | o | x | o | bw | SO2 | yes |
| 67 | 25 | x | x | o | x | x | o | o | o | x | bw | SO2 | yes |
| 68 | 26 | x | x | n | x | x | o | o | o | o | bw | SO2 | yes |
| 69 | 27 | x | x | n | x | x | o | x | x | x | bw | SO2 | yes |
| 70 | 28 | x | x | n | x | x | x | x | x | x | bw | SO2 | yes |
| 71 | 29 | x | x | o | x | x | o | o | o | o | AHC | SO2 | yes |
| 72 | 30 | x | x | o | x | x | o | x | o | o | AHC | SO2 | yes |
| 73 | 31 | x | x | o | x | x | o | o | x | o | AHC | SO2 | yes |
| 74 | 32 | x | x | o | x | x | o | o | o | x | AHC | SO2 | yes |
| 75 | 33 | x | x | n | x | x | o | o | o | o | AHC | SO2 | yes |
| 76 | 34 | x | x | n | x | x | o | x | x | x | AHC | SO2 | yes |
| 77 | 35 | x | x | n | x | x | x | x | x | x | AHC | SO2 | yes |
| 78 | 36 | x | x | o | x | x | o | o | o | o | NH3 | SO2 | yes |
| 79 | 37 | x | x | o | x | x | o | x | o | o | NH3 | SO2 | yes |
| 80 | 38 | x | x | o | x | x | o | o | x | o | NH3 | SO2 | yes |
| 81 | 39 | x | x | o | x | x | o | o | o | x | NH3 | SO2 | yes |
| 82 | 40 | x | x | n | x | x | o | o | o | o | NH3 | SO2 | yes |
| 83 | 41 | x | x | n | x | x | o | x | x | x | NH3 | SO2 | yes |
| 84 | 42 | x | x | n | x | x | x | x | x | x | NH3 | SO2 | yes | x = is carried out
n = is not carried out
o = optional
AHC = ammonium hydrogencarbonate
NH3 = ammonia
SO2 = sulfur dioxide
bw = base freely chooseable within the disclosure
sw = sulfur component freely chooseable within the disclosure

What is claimed is:

1. A process for producing a vinyllactam polymer having K values of 10 to 150, the process comprising the steps in the sequence set forth:
   a) polymerizing one or more N-vinyllactams and optionally further monomers via free-radical polymerization with a free-radical initiator in an aqueous liquid, wherein the polymerization process is performed as batch process, as semi-batch process or as continuous process;
   b) using at least one base to maintain the pH during the polymerization in a range from 5 to 11;
   c) optional postpolymerization, wherein a further initiator is added;
   d) optional purification by stripping with gas, thermal distillation and/or steam distillation;
   e) treating the vinyllactam polymer with a sulfur component selected from the group consisting of sulfurous acid, sulfur dioxide and one or more salts of sulfurous acid, wherein the pH of a water-containing phase with which the polymer comes into contact during the treatment with the sulfur component has a value of less than 6, and keeping the polymer in contact with the water-containing phase comprising the sulfur component at this pH for a period between 10 minutes and 5 hours, and then optional repeat of step d);
   f) optionally adding at least one base to set a desired pH in the range from 4 to 9;
   g) optional purification by filtering; and
   h) optional drying to form a free-flowing powder.

2. The process according to claim 1, wherein step f) utilizes a base selected from the group consisting of ammonia, ammonium (hydrogen)carbonate, 2-amino-2-methyl-1-propanol, tris(hydroxymethyl)aminomethane, triethylamine or triethanolamine.

3. The process according to claim 1, wherein step g) utilizes a mechanical filter.

4. The process according to claim 1, wherein step h) utilizes a spray-drying process or a contact-drying process to obtain a dry polymeric powder.

5. The process according to claim 1, wherein no postpolymerization (step c)) is carried out.

6. The process according to claim 1, wherein step f) utilizes a base selected from the group consisting of ammonia, ammonium (hydrogen)carbonate, 2-amino-2-methyl-1-propanol, tris(hydroxymethyl)aminomethane, triethylamine or triethanolamine, step g) utilizes a mechanical filter and step h) utilizes a spray-drying process or a contact-drying process.

7. The process according to claim 1, wherein no postpolymerization (step c)) is carried out, step f) utilizes a base selected from the group consisting of ammonia, ammonium (hydrogen)carbonate, 2-amino-2-methyl-1-propanol, tris (hydroxymethyl)aminomethane, triethylamine or triethanolamine, step g) utilizes a mechanical filter and step h) utilizes a spray-drying process or a contact-drying process, and a further purification step d) is carried out after step e).

8. The process according to claim 1, wherein the base used in step b) is ammonium hydrogencarbonate, ammonium carbonate, 2-amino-2-methyl-1-propanol or ammonia.

9. The process according to claim 1, wherein the sulfur component used in step e) is sulfur dioxide in aqueous solution.

10. The process according to claim 1, wherein the process only consists of steps a) to h) including the optional repeat of step d) after step e) and no further steps are included.

11. The process according to claim 1, wherein no purification by stripped (step d)) is carried out.

12. A process for producing a vinyllactam polymer having K values of 10 to 150, the process comprising the steps in the sequence set forth:
   a) polymerizing one or more N-vinyllactams and optionally further monomers via free-radical polymerization with a free-radical initiator in an aqueous liquid, wherein the polymerization process is performed as batch process, as semi-batch process or as continuous process;
   b) using at least one base to maintain the pH during the polymerization in a range from 5 to 11;
   c) optional postpolymerization, wherein a further initiator is added;
   d) purification by stripping with gas, thermal distillation and/or steam distillation;
   e) treating the vinyllactam polymer with a sulfur component selected from the group consisting of sulfurous acid, sulfur dioxide and one or more salts of sulfurous acid, wherein the pH of a water-containing phase with which the polymer comes into contact during the treatment with the sulfur component has a value of less than 6, and keeping the polymer in contact with the water-containing phase comprising the sulfur component at this pH for a period between 10 minutes and 5 hours, and then optional repeat of step d);
   f) optionally adding at least one base to set a desired pH in the range from 4 to 9;
   g) optional purification by filtering; and
   h) optional drying to form a free-flowing powder.

* * * * *